(12) United States Patent
Tang et al.

(10) Patent No.: US 11,220,629 B2
(45) Date of Patent: Jan. 11, 2022

(54) TWO-PHOTON FLUORESCENT COMPOUNDS FOR SPECIFIC LIPID DROPLET IMAGING IN LIVE CELLS AND DEEP TISSUES AT ULTRALOW CONCENTRATION

(71) Applicant: THE HONG KONG UNIVERSITY OF SCIENCE AND TECHNOLOGY, Hong Kong (CN)

(72) Inventors: Benzhong Tang, Hong Kong (CN); Guangle Niu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 15 days.

(21) Appl. No.: 16/961,569

(22) PCT Filed: Jan. 11, 2019

(86) PCT No.: PCT/CN2019/071262
§ 371 (c)(1),
(2) Date: Jul. 10, 2020

(87) PCT Pub. No.: WO2019/137449
PCT Pub. Date: Jul. 18, 2019

(65) Prior Publication Data
US 2021/0062079 A1    Mar. 4, 2021

Related U.S. Application Data

(60) Provisional application No. 62/709,249, filed on Jan. 11, 2018.

(51) Int. Cl.
  *C09K 11/06*   (2006.01)
  *C07C 255/43*  (2006.01)
  (Continued)

(52) U.S. Cl.
  CPC ............ *C09K 11/06* (2013.01); *C07C 255/43* (2013.01); *C07D 213/57* (2013.01);
  (Continued)

(58) Field of Classification Search
  None
  See application file for complete search history.

(56) References Cited

U.S. PATENT DOCUMENTS 10,753,941 B2 *   8/2020   Tang ................. A61K 49/0054

FOREIGN PATENT DOCUMENTS

CN   107192695 A   9/2017
CN   107200709 A   9/2017

* cited by examiner

*Primary Examiner* — Edwin C Gunberg
(74) *Attorney, Agent, or Firm* — Nath, Goldberg & Meyer; Joshua B. Goldberg

(57) ABSTRACT

Fluorescent compounds that have aggregation-induced emission (AIE) characteristics. The compounds can be utilized as lipid droplet (LD)-specific bio-probes in cell imaging, with high photostability and brightness. For example, the compounds can be used for specific two-photon LDs staining in live cells and deep-tissues at ultralow concentrations. The compounds exhibit a large Stokes shift (>110 nm), high solid fluorescence quantum yields (up to 0.30), a good two-photon absorption cross-section (45-100 GM at 860 nm), high biocompatibility, and good photostability.

20 Claims, 20 Drawing Sheets

(51) Int. Cl.
*C07D 213/57* (2006.01)
*G01N 21/64* (2006.01)
*G02B 21/00* (2006.01)

(52) U.S. Cl.
CPC ..... *G01N 21/6428* (2013.01); *G01N 21/6458* (2013.01); *G02B 21/0076* (2013.01); *C09K 2211/1007* (2013.01); *C09K 2211/1011* (2013.01); *C09K 2211/1018* (2013.01); *G02B 21/0032* (2013.01); *G02B 2207/114* (2013.01)

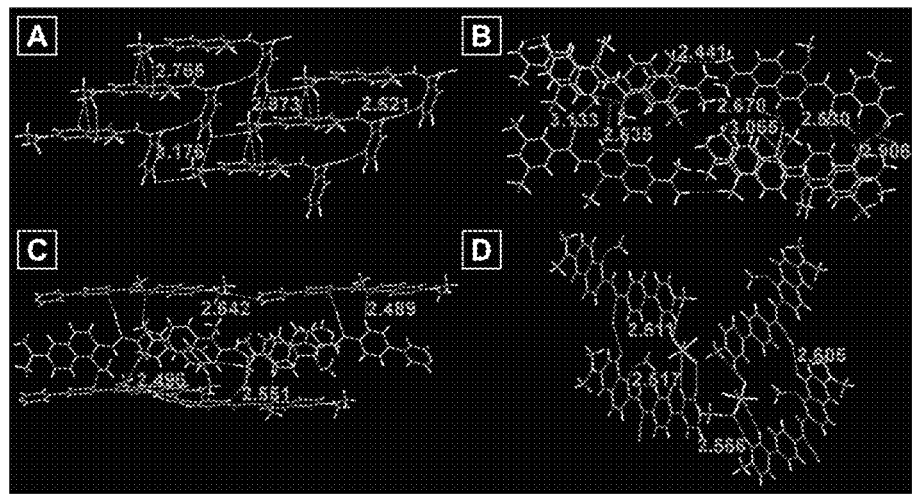
Figs. 3A-3D
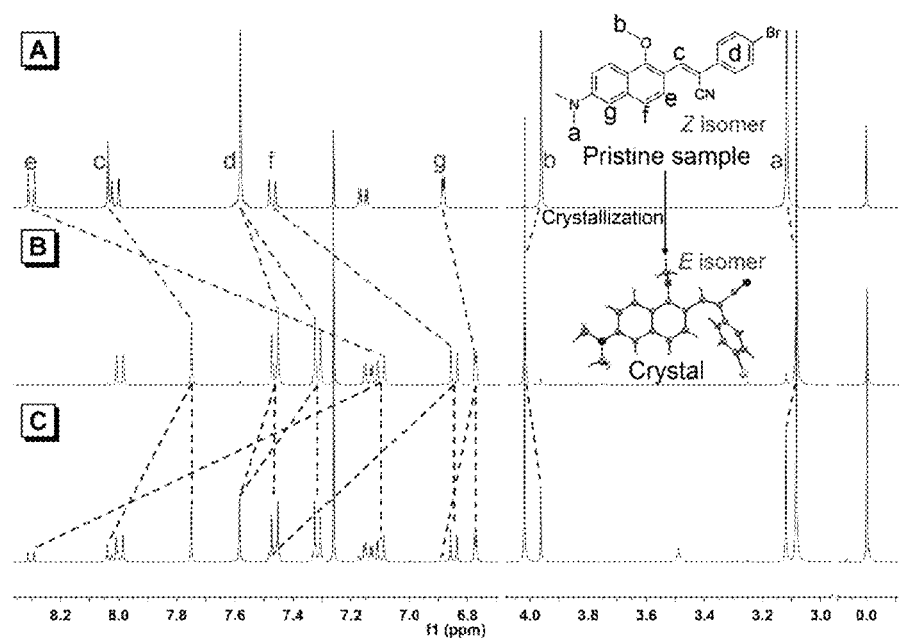
Figs. 4A-C

C₂₂H₁₉BrN₂O
Calcd 406.0681 [M]
Found 406.0691

TWO-PHOTON FLUORESCENT COMPOUNDS FOR SPECIFIC LIPID DROPLET IMAGING IN LIVE CELLS AND DEEP TISSUES AT ULTRALOW CONCENTRATION

CROSS-REFERENCE

The present application claims priority to provisional U.S. Patent Application No. 62/709,249, filed Jan. 11, 2018, which was filed by the inventors hereof and is incorporated herein by reference in its entirety.

FIELD

The present subject matter relates generally to a series of fluorescent compounds with aggregation-induced emission characteristics and their applications in imaging of lipid droplets in live cells and deep tissues at ultralow concentrations.

BACKGROUND

Lipid droplets (LDs) are ubiquitous lipid-rich spherical organelles in most cells and organisms. LDs mainly contain triglycerides and cholesterol esters and are enclosed by a phospholipid monolayer with specific proteins. LDs, as dynamic organelles, are involved in many cellular functions, such as lipid metabolism, membrane synthesis and transfer, signal transduction, and protein degradation. Recent studies have shown that LDs are also highly associated with obesity, diabetes, inflammatory disorders and cancer. Some imaging techniques, such as transmission electron microscopy, Raman microscopy, and immunofluorescence microscopy, have been utilized to visualize LDs. Generally, however, these imaging techniques suffer from complicated procedures, poor cellular permeability, and interfere with cell function. Therefore, the development of effective methods for direct and selective LDs visualization and monitoring in biological samples containing live cells and live tissues is of great importance.

Fluorescence imaging has become an indispensable tool for visualizing the localization and the dynamics of cellular compartments and molecular processes due to its excellent selectivity, remarkable sensitivity and extraordinary temporal/spatial resolution. Compared with one-photon fluorescence imaging, two-photon (TP) fluorescence imaging, which utilizes two near-infrared (NIR) photons as the excitation source, are highly favored in biomedical imaging because of deeper tissue penetration, higher spatial resolution, lower background fluorescence, and lower photodamage and photobleaching.

Nile Red and BODIPY 493/503, conventional fluorescent dyes for LDs staining, suffer from many drawbacks. Nile Red shows unfavorable background staining and broad emission, which limits its application in multicolor imaging. BODIPY 493/503 exhibits very small Stokes shifts and, thus, induces nonradiative energy and interference from scattered light. Further, the incubation concentrations of the conventional dyes for LDs staining are normally in the range of 5-10 μM or even higher. These conventional organic fluorophores also encounter the detrimental phenomenon of aggregation-caused quenching (ACQ) at such high concentrations. Specifically, these conventional fluorophores typically emit strongly when in solution, but experience emission quenching upon aggregate formation due to intermolecular π-π stacking and other non-radiative pathways. The few dyes which have previously been synthesized for LDs imaging at nano-molar concentrations showed nonspecific staining and exhibited blue emission in live cells, resulting in low signal-to-noise ratio. These ACQ-based dyes also showed small Stokes shifts and their photostabilities were concerning. Further, TP deep-tissue imaging based on these dyes has rarely been explored.

Unlike the ACQ-based dyes, aggregation-induced emission (AIE) luminogens are non-emissive or weakly emissive in solution, but are typically induced to fluoresce intensely once aggregated through restriction of intramolecular motions (RIM). As a result, AIE fluorophores can be effective at high concentrations and in the aggregated state, emitting bright fluorescence and having a high photobleaching threshold.

Accordingly, fluorescent AIEgens which can be used as LDs-specific bio-probes are highly desirable.

SUMMARY

The present subject matter relates to fluorescent compounds that have aggregation-induced emission (AIE) characteristics. The compounds can be utilized as lipid droplet (LD)-specific bio-probes in cell imaging, with high photostability and brightness. For example, the compounds can be used for specific two-photon LD staining in live cells and deep tissues at ultralow concentrations. The compounds exhibit a large Stokes shift (>110 nm), high solid fluorescence quantum yields (up to 0.30), a good two-photon absorption cross-section (45-100 GM at 860 nm), high biocompatibility, and good photostability. As described herein, use of the present compounds in in vitro and ex vivo two-photon imaging of LDs in live cells and live mice liver tissues was successfully demonstrated. LDs were successfully visualized in live mice liver tissues at a depth of about 70 μm. In addition, semi-theoretical data of calculated log P(C log P) values revealed that the compounds can specifically locate in LDs.

In an embodiment, the compounds have the following backbone structural formula:

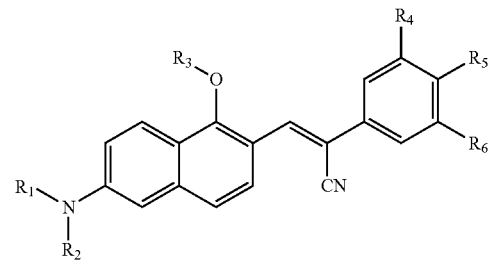

wherein $R_1$, $R_2$, and $R_3$ are independently selected from the group consisting of $C_nH_{2n+1}$, $C_6H_5$, $C_{10}H_7$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$ and

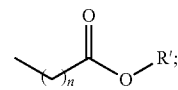

wherein R' is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

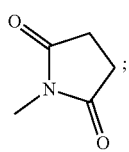

wherein $R_4$, $R_5$, and $R_6$ are independently selected from the group consisting of H, $CH_3$, F, Cl, Br, I, CN, $CF_3$, $NO_2$, phenyl, pyridyl, CH=CHPh, and C≡CPh; and wherein n is an integer ranging from 1 to 10.

In a further embodiment, the compounds include one or more compounds selected from the group consisting of:

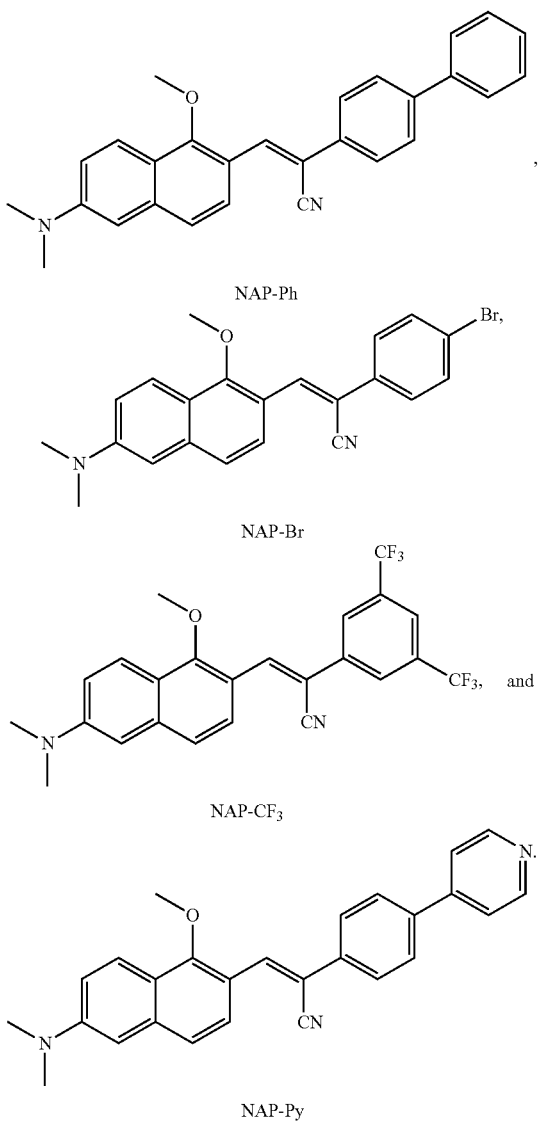

BRIEF DESCRIPTION OF DRAWINGS

Various embodiments will now be described in detail with reference to the accompanying drawings.

FIG. 3A depicts principal intermolecular packing interactions of NAP-Br. FIG. 3B depicts principal intermolecular packing interactions of NAP-$CF_3$. FIG. 3C depicts principal intermolecular packing interactions of NAP-Py. FIG. 3D depicts principal intermolecular packing interactions of NAP-Py$^+$ (Distances in Å).

FIG. 4A depicts $^1$H NMR spectra changes of NAP-Br in amorphous state (Z isomer). FIG. 4B depicts $^1$H NMR spectra changes of NAP-Br in crystal state (E isomer). FIG. 4C depicts the $^1$H NMR spectra which was obtained by solvent evaporation of the E isomer (FIG. 4B) followed by redissolution of the obtained solids in $CDCl_3$.

DETAILED DESCRIPTION

Figure 1:
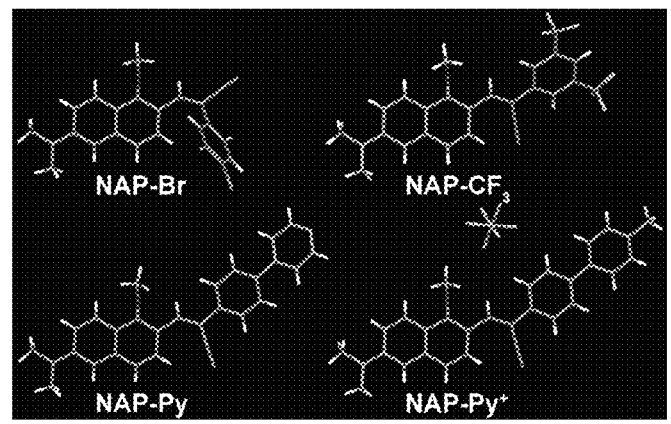
FIG. 1 depicts the single crystal structures of NAP-Br, NAP-$CF_3$, NAP-Py, and NAP-Py$^+$.

The following definitions are provided for the purpose of understanding the present subject matter and for constructing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise.

It should be understood that the order of steps or order for performing certain actions is immaterial so long as the present teachings remain operable. Moreover, two or more steps or actions may be conducted simultaneously.

The term "$\lambda_{ex}$" as used herein refers to excitation wavelength.

The term "Ph" as used herein refers to phenyl.

The term "Py" as used herein refers to pyridyl.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

"Emission intensity" as used herein refers to the magnitude of fluorescence/phosphorescence normally obtained from a fluorescence spectrometer or fluorescence microscopy measurement; "fluorophore" or "fluorogen" as used herein refers to a molecule which exhibits fluorescence; "luminogen" or "luminophore" as used herein refers to a molecule which exhibits luminescence; and "AIEgen" as used herein refers to a molecule exhibiting AIE characteristics.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl,-pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine Noxide thiophene S-oxide, thiophene S,S-dioxide). Examples of heteroaryl groups include, for example, the 5- or 6-membered monocyclic and 5-6 bicyclic ring systems shown below:

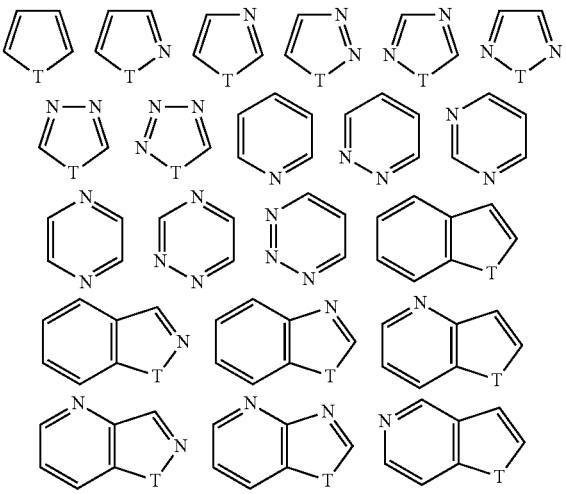

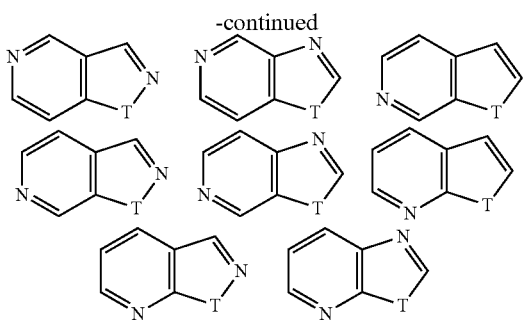

where T is O, S, NH, N-alkyl, N-aryl, N-(arylalkyl) (e.g., N-benzyl), SiH2, SiH(alkyl), Si(alkyl)2, SiH(arylalkyl), Si(arylalkyl)2, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, a "donor" material refers to an organic material, for example, an organic nanoparticle material, having holes as the majority current or charge carriers.

As used herein, an "acceptor" material refers to an organic material, for example, an organic nanoparticle material, having electrons as the majority current or charge carriers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Fluorescent Compounds

The present subject matter contemplates fluorescent compounds having aggregation-induced emission (AIE) characteristics. The present compounds, also referred to as "NAP AIEgens" herein, include a naphthalene unit and possess conjugated donor-acceptor (D-A) structures. The compounds exhibit large Stokes shifts (>110 nm), high solid fluorescence quantum yields (up to 0.30) and good two-photon absorption cross-section (45-100 GM at 860 nm). The compounds can be used for specific two-photon lipid droplet (LD) staining in live cells and live deep tissues. As described in detail herein, the compounds show specific lipid droplets (LDs) staining in live cells with high signal-to-noise ratio at nano-molar or ultralow concentrations (50 nM or less). In addition, semi-theoretical data of calculated log P (C log P) values revealed that these lipophilic compounds can specifically locate in LDs. With the present compounds, LDs in live tissues can be visualized with a high signal-to-noise ratio at depths as high as about 70 μm using two-photon specific imaging. The present compounds also exhibit high biocompatibility and good photostability.

In an embodiment, the compounds have the following backbone structural formula:

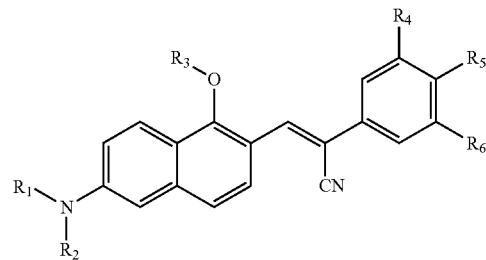

wherein $R_1$, $R_2$, and $R_3$ are independently selected from the group consisting of $C_nH_{2n+1}$, $C_6H_5$, $C_{10}H_7$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$ and

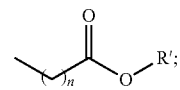

wherein R' is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

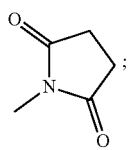

wherein $R_4$, $R_5$, and $R_6$ are independently selected from the group consisting of H, $CH_3$, F, Cl, Br, I, CN, $CF_3$, $NO_2$, Ph, Py, CH=CHPh, and C≡CPh; and wherein n is an integer ranging from 1 to 10.

In a further embodiment, the compound includes one or more compounds selected from the group consisting of:

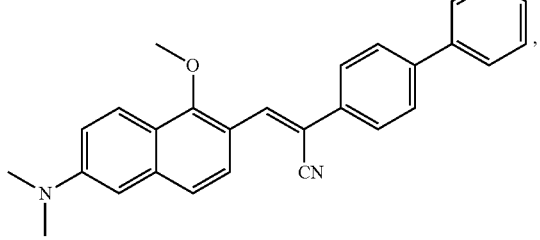

NAP-Ph

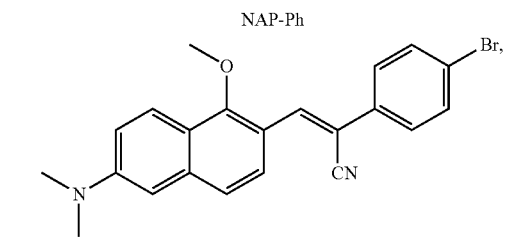

NAP-Br

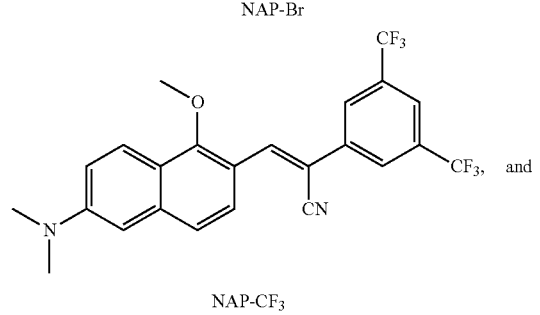

NAP-$CF_3$, and

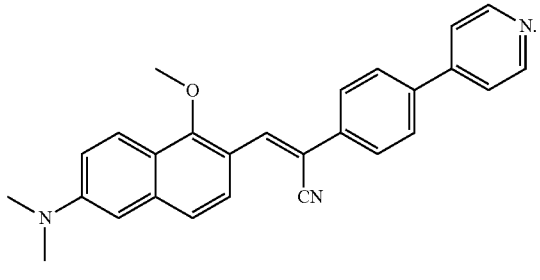

NAP-Py

Exemplary reaction schemes for preparing NAP-Ph, NAP-Br, NAP-$CF_3$, NAP-Py, and NAP-$Py^+$ are provided below:

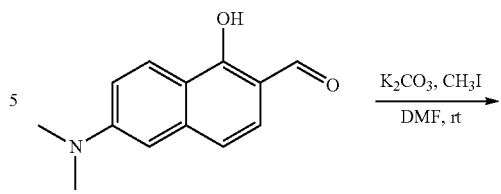

1

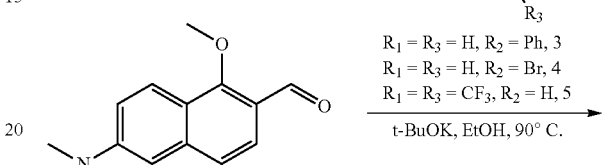

$R_1 = R_3 = H$, $R_2 = Ph$, 3
$R_1 = R_3 = H$, $R_2 = Br$, 4
$R_1 = R_3 = CF_3$, $R_2 = H$, 5 t-BuOK, EtOH, 90° C.

2

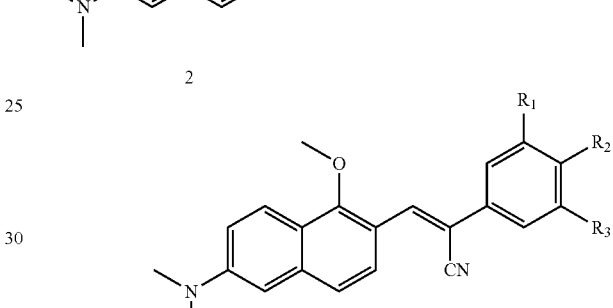

$R_1 = R_3 = H$, $R_2 = Ph$, NAP—Ph
$R_1 = R_3 = H$, $R_2 = Br$, NAP—Br
$R_1 = R_3 = CF_3$, $R_2 = H$, NAP—$CF_3$

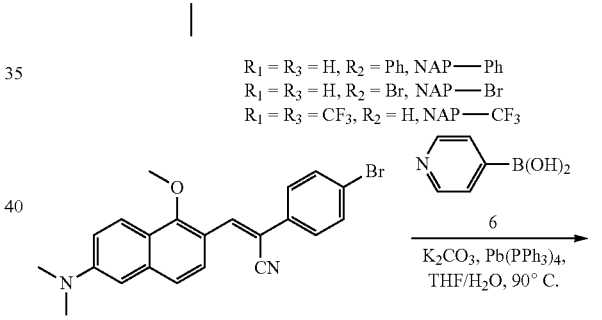

NAP—Br $K_2CO_3$, Pb(PPh$_3$)$_4$, THF/$H_2O$, 90° C.

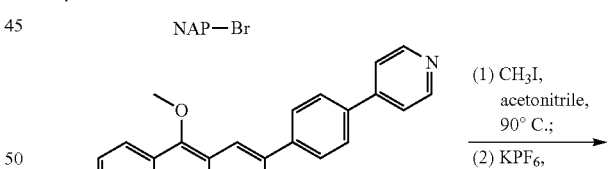

NAP—Py (1) $CH_3I$, acetonitrile, 90° C.;
(2) $KPF_6$, acetone, rt

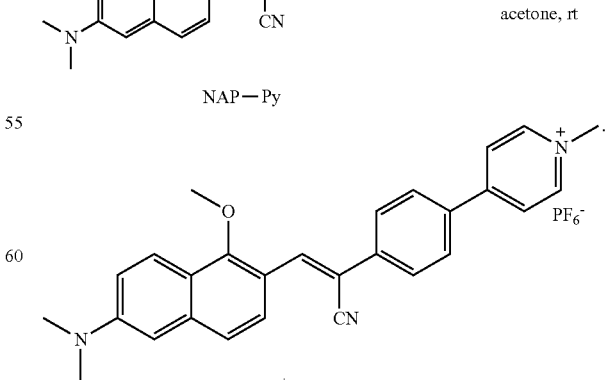

NAP—$Py^+$

Cell Imaging

An abnormality in lipid droplets (LDs) of a cell is a critical biomarker for diseases, such as cancer, diabetes, obesity, fatty liver disease, and inflammatory disorders. The fluorescent compounds described herein can specifically target LDs in live cells and live tissues and provide efficient fluorescent probes of the lipid droplets for diagnostic purposes.

The present compounds are lipophilic compounds. Due to the presence of triglycerides and cholesterol esters in LDs, the inherent environment of LDs is also lipophilic. Without being limited to any specific mechanism of action, it is believed that the lipid droplet staining specificity of the present compounds can be attributed to like-like interactions resulting from accumulation of the fluorescent compounds in the hydrophobic lipid droplets. While donor-acceptor (D-A) based organic dyes with increased acceptor ability generally show red-shifted fluorescence, more hydrophobicity and larger two-photon absorption cross section, a balance between hydrophobicity and cell penetrability has previously been difficult to achieve. The present naphthalene-based, D-A compounds described herein can effectively be used for specific LDs visualization in live cells and live tissues at ultralow concentration, e.g., nano-molar levels.

The fluorescent compounds can be contacted with a target cell and an imaging method can then be used to visualize a target of interest in the target cell. The target of interest can be lipid droplets. The imaging method can include, for example, fluorescence microscopy or confocal laser scanning microscopy. The fluorescence microscopy can include two-photon fluorescence imaging. The target cell can be a live cell. The target cell can be in live tissue. A concentration of the compounds can be 50 nM or less.

The present teachings are illustrated by the following examples.

EXAMPLES

Materials and Instruments

Dulbecco's Modified Essential Medium (DMEM) was purchased from Gibco (Life Technologies). Ultrapure water was supplied by Milli-Q Plus System (Millipore Corporation, United States). Phosphate buffered saline (PBS), fetal bovine serum (FBS), penicillin, streptomycin, and BODIPY 493/503 were purchased from Thermo Fisher Scientific. Other reagents used in this work were purchased from Sigma-Aldrich and used as received without further purification. All the chemicals used in the synthesis of AIEgens were purchased from Sigma-Aldrich.

$^1$H and $^{13}$C NMR spectra were measured on Bruker ARX 400 NMR spectrometers using $CDCl_3$ as the deuterated solvent. High-resolution mass spectra (HRMS) were recorded on a Finnegan MAT TSQ 7000 Mass Spectrometer System operating in a MALDI-TOF mode. UV absorption spectra were taken on a Milton Ray Spectronic 3000 array spectrophotometer. Steady-state fluorescence spectra were recorded on a Perkin Elmer LS 55 spectrometer. Fluorescence images were collected on Olympus BX 41 fluorescence microscope. Laser confocal scanning microscope images were collected on Zeiss laser scanning confocal microscope (LSM7 DUO) and analyzed using ZEN 2009 software (Carl Zeiss). Two-photon fluorescence imaging was carried out on Olympus FV 300 laser confocal microscope. In two-photon experiments, the excitation wavelengths were 860 nm from a Ti:sapphire femtosecond laser source (coherent chamelon ultra) and the incident power on samples was modified by means of an attenuator and examined with a power monitor (Coherent). A multiphoton emission filter (FF01-750; Semrock) was used to block the IR laser.

Example 1

Crystal Structure Analysis

Figures 2A, 2B, 2C, 2D, 2E:
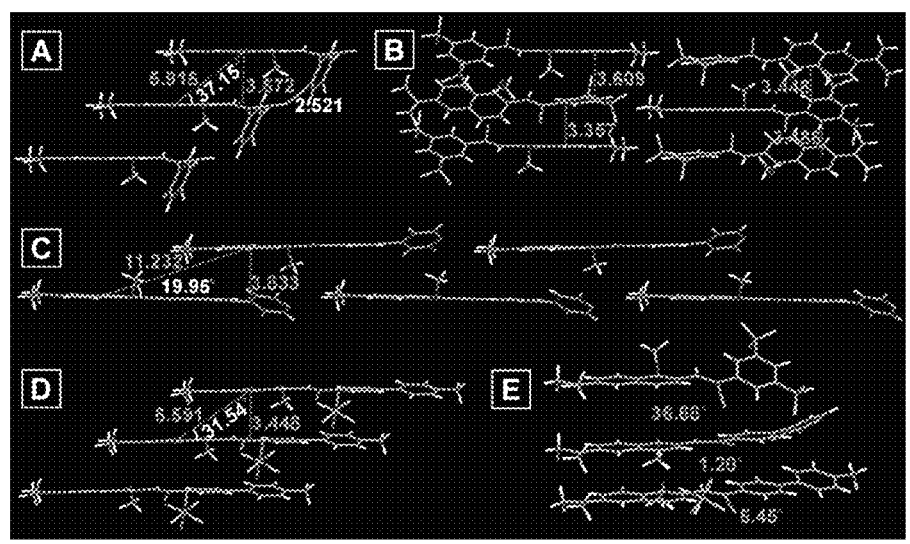
FIG. 2A depicts molecular packing in the crystal structure of NAP-Br.
FIG. 2B depicts molecular packing in the crystal structure of NAP-$CF_3$.
FIG. 2C depicts molecular packing in the crystal structure of NAP-Py.
FIG. 2D depicts molecular packing in the crystal structure of NAP-Py$^+$.
FIG. 2E depicts dihedral angles between naphthalene and benzene of NAP-$CF_3$, NAP-Py, and NAP-Py$^+$ (Distances in Å).

The structures of NAP-Ph, NAP-Br, NAP-CF$_3$, NAP-Py, and NAP-Py$^+$ were verified by $^1$H NMR, $^{13}$C NMR, and MALDI-TOF-HRMS spectroscopy (FIGS. 22-38). The crystal structures of NAP-Br, NAP-CF$_3$, NAP-Py, and NAP-Py$^+$ were confirmed by X-ray crystal structure analysis (FIGS. 1-4). Single crystals of NAP-Br, NAP-CF$_3$, NAP-Py, and NAP-Py$^+$ suitable for X-ray structure analysis were obtained by slow evaporation of mixed solvent of $CH_2Cl_2$ and MeOH ($CH_2Cl_2$/MeOH=3:1, v/v) at ambient temperature. The crystal of NAP-Br is the E isomer (FIG. 4), the structure of which was verified by $^1$H NMR spectroscopy. NAP-CF$_3$ has intramolecular π-π interaction while NAP-Br, NAP-Py, and NAP-Py$^+$ exhibit π-π stacking interactions (FIGS. 2A-E). There exist multiple intramolecular interactions to stabilize the different packing modes of NAP-CF$_3$, NAP-Py, and NAP-Py$^+$, such as C—H . . . O, C—H . . . N, C—H . . . F and C—F . . . F interactions (FIGS. 3A-3D), which can help to restrict the intramolecular motion and block the non-radiative processes in the aggregated state. The C—H . . . N interaction is likely the main driving force for the formation of crystals of E isomer of NAP-Br. The molecules of NAP-Br, NAP-Py, and NAP-Py$^+$ in the crystal lattice are arranged in a head-to-tail arrangement (FIGS. 2A, C and D), which probably formed J-aggregation. Previous studies show that the angle ($0°<θ_1<54.7°$) between the molecular plane and the aggregation direction demonstrates J-aggregation. As shown, the angle $θ_1$ is 37.15°, 19.95° and 31.54° for NAP-Br, NAP-Py, and NAP-Py$^+$ (FIGS. 2A, C and D), respectively, demonstrating that these three AIEgens do form J-aggregation. Unlike NAP-Py and NAP-Py$^+$, NAP-CF$_3$ only showed intermolecular π-π interaction rather than J-aggregation in molecule packing probably because NAP-Py and NAP-Py$^+$ have excellent planarity while the molecule of NAP-CF$_3$ is highly twisted (FIG. 2E). The dihedral angles $θ_2$ between naphthalene and benzene in NAP-CF$_3$, NAP-Py, and NAP-Py$^+$ are 36.68°, 1.20° and 5.45°, respectively (FIG. 2E).

Example 2

Photophysical Properties

The absorption and fluorescence (FL) data of the NAP AIEgens were investigated, and corresponding spectra are shown in FIGS. 5A-5H, 6A-6E, and FIG. 7. The data are summarized in Table 1 below.

TABLE 1

Photophysical properties of NAP AIEgens

| | THF or CH$_3$CN | | | | | Solid | | | |
|---|---|---|---|---|---|---|---|---|---|
| | $\lambda_{abs}^{max}$ (nm) | $\lambda_{em}^{max}$ (nm) | Stokes shift (nm) | $\Phi$ | $\tau$ (ns) | $\lambda_{em}^{max}$ (nm) | $\Phi$ | $\tau$ (ns) | $\alpha_{AIE}^{b}$ |
| NAP-Ph | 409 | 523 | 114 | 0.018 | <0.34 | 566 | 0.268 | 1.42 | 14.89 |
| NAP-Br | 409 | 525 | 116 | 0.014 | <0.60 | 597 | 0.126 | 4.43 | 9.00 |
| NAP-CF$_3$ | 425 | 560 | 135 | 0.016 | <0.67 | 555 | 0.292 | 6.29 | 18.25 |
| NAP-Py | 413 | 541 | 128 | 0.015 | <0.67 | 619 | 0.217 | 1.39 | 14.47 |
| NAP-Py$^{+a}$ | 455 | 540 | 85 | 0.008 | <0.58 | 676 | 0.048 | 1.32 | 6.00 |

$^a$Due to the solubility of NAP-Py$^+$, CH$_3$CN was chosen as the solvent.
$^b\alpha_{AIE} = \Phi_{solid}/\Phi_{solvent}$.

Figures 5A, 5B, 5C, 5D, 5E, 5F, 5G, 5H:
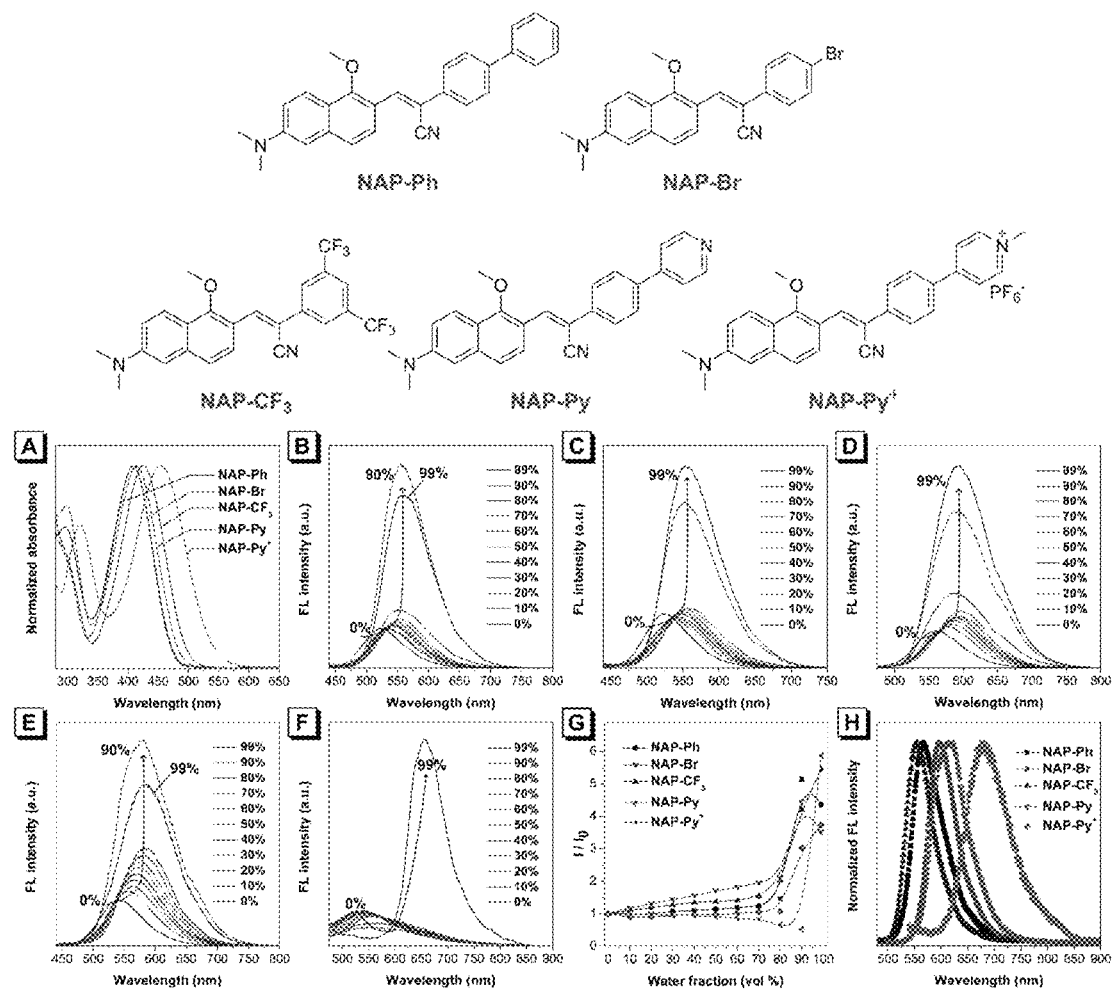
FIG. 5A depicts normalized absorption spectra of NAP AIEgens (10 μM) in THF or $CH_3CN$.
FIG. 5B depicts fluorescence spectra of NAP-Ph (10 μM) in THF and THF/water mixture with different water fractions.
FIG. 5C depicts fluorescence spectra of NAP-Br (10 μM) in THF and THF/water mixture with different water fractions.
FIG. 5D depicts fluorescence spectra of NAP-$CF_3$ (10 μM) in THF and THF/water mixture with different water fractions.
FIG. 5E depicts fluorescence spectra of NAP-Py (10 μM) in THF and THF/water mixture with different water fractions.
FIG. 5F depicts fluorescence spectra of NAP-Py$^+$ (10 μM) in $CH_3CN$ and $CH_3CN$/water mixture with different water fractions.
FIG. 5G depicts plots of relative maximum emission intensity ($I/I_0$) of NAP AIEgens (10 μM) versus the solvent composition of THF/water mixture or $CH_3CN$/water mixture.
FIG. 5H depicts normalized fluorescence spectra of NAP AIEgens in the solid state. (Due to the solubility of NAP-Py$^+$, $CH_3CN$ was chosen as the organic solvent).
Figures 6A, 6B, 6C, 6D, 6E:
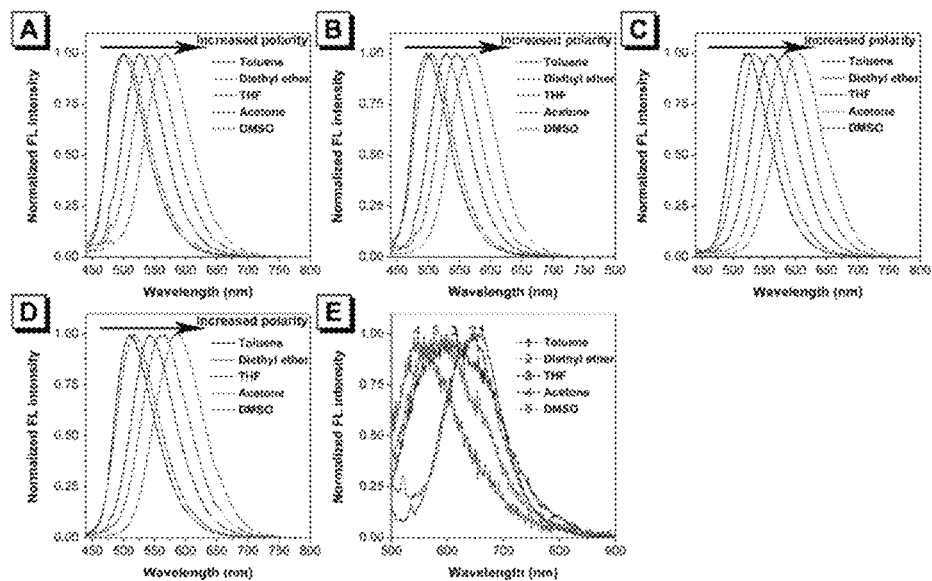
FIG. 6A depicts fluorescence spectra of NAP-Ph in different polar solvents.
FIG. 6B depicts fluorescence spectra of NAP-Br in different polar solvents.
FIG. 6C depicts fluorescence spectra of NAP-$CF_3$ in different polar solvents.
FIG. 6D depicts fluorescence spectra of NAP-Py in different polar solvents.
FIG. 6E depicts fluorescence spectra of NAP-Py$^+$ in different polar solvents.
Figure 7:
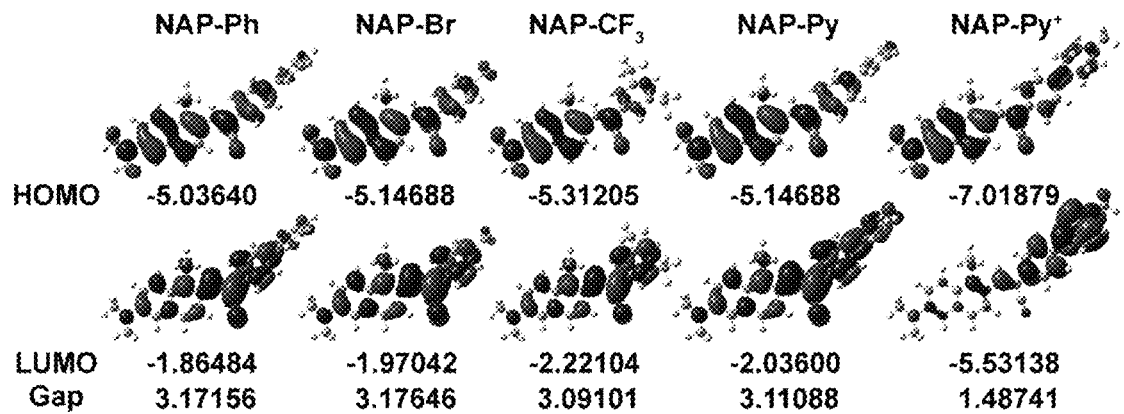
FIG. 7 depicts spatial distributions of calculated HOMOs and LUMOs and HOMO/LUMO energy gaps (units, eV) of NAP AIEgens.

NAP-Ph showed an absorption peak ($\lambda_{abs}^{max}$) at 409 nm in dilute THF solution and a weak emission peak ($\lambda_{em}^{max}$) at 523 nm (FIGS. 5A-5B). In the THF/water mixtures, its emission showed a slight red shift with increased water fraction ($f_w$), and its emission intensity first decreased ($f_w$<20%) and then increased ($f_w$>20%). When the water fraction ($f_w$) increased to 90%, the emission ($\lambda_{em}^{max}$=557 nm) of NAP-Ph showed a significant enhancement due to the formation of aggregates (FIG. 5B), which indicated that NAP-Ph exhibits the aggregation-enhanced emission (AEE) property. With further increased water fraction ($f_w$=99%), the emission intensity gradually decreased, which is an often-observed phenomenon for AIEgens. This phenomenon is probably due to the changes in morphology and size of the aggregates formed in the water-THF mixture with high water fractions. Likewise, NAP-Br, NAP-CF$_3$, NAP-Py, and NAP-Py$^+$ also showed AEE properties as investigated by FL spectra (FIG. 5C-5F). It should be noted that the FL of NAP AIEgens in high water fraction ($f_w$>90%) increased only several-fold compared with that in THF or CH$_3$CN (FIG. 5G), probably because of formation of loosely packed aggregates. NAP AIEgens exhibit donor-acceptor structures and showed increased acceptor ability (NAP-Py$^+$>NAP-CF$_3$>NAP-Py>NAP-Br>NAP-Ph), and the absorption peak of NAP AIEgens showed a red shift. The FL spectra of NAP AIEgens were further measured in different polar solvents (FIGS. 6A-6E). The maximal emission wavelengths of NAP-Ph, NAP-Br, NAP-CF$_3$, and NAP-Py gradually increased from toluene, diethyl ether, THF, acetone to DMSO, indicating the phenomenon of positive solvatochromism. However, NAP-Py$^+$ showed negative solvatochromism. Compared with FL in THF or CH$_3$CN, solid FL (FL of 555-676 nm, FIG. 3D and Table 1) of NAP AIEgens except for NAP-CF$_3$ showed red shift, probably due to the formation of J-aggregation (FIGS. 2A, C and D). As for NAP-CF$_3$, the reason for blue-shifted FL in the solid state was likely its twisted structure (FIG. 2E), resulting in only intramolecular π-π interaction rather than J-aggregation (FIG. 2B). It is worth mentioning that NAP AIEgens exhibited large Stokes shifts (Table 1), which could reduce self-absorption, thereby affording high resolution and facilitate multi-channel bio-imaging. The FL quantum yields (QYs, Table 1) of NAP AIEgens were measured by using an integrating sphere. NAP AIEgens showed weak emission in organic solvents (THF or CH$_3$CN), possibly because intramolecular motion can enhance the non-radiative processes; however, intramolecular motion in the solid state can be restricted due to multiple intramolecular interactions (FIG. 3), resulting in high FL QYs. It should be pointed out that the solid FL QY of NAP-Py$^+$ was low, likely due to a narrow energy gap and enhanced nonradiative transitions in NIR fluorescent dyes (FIG. 7). Furthermore, longer FL lifetimes of NAP AIEgens in the solid state than those in solvents also verified that restriction of intramolecular motion (RIM) can prohibit energy dissipation via non-radiative channels and enhance the FL of NAP AIEgens (Table 1).

DFT calculations were performed at the B3LYP/6-31G level of theory by using the Gaussian 09 program package to further investigate the optical properties of NAP AIEgens. The calculated HOMOs and LUMOs of NAP AIEgens are shown in FIG. 7. The electron densities of HOMOs of NAP AIEgens were mainly located throughout the whole molecules especially in the part of N,N-dimethylamino-substituted naphthalene, while the electron densities of LUMOs of NAP AIEgens were mainly located in the part of cyanostilbene (FIG. 7). The electron densities of HOMOs and LUMOs of NAP-Py$^+$ showed obvious separation, likely due to its strong ICT effect. NAP AIEgens exhibited donor-acceptor structures and with increased acceptor ability (NAP-Py$^+$>NAP-CF$_3$>NAP-Py>NAP-Br>NAP-Ph), the HOMO and LUMO energy levels were decreased due to the electron-withdrawing groups, resulting in a narrower energy gap and red-shifted absorption (FIG. 7), which was in good accordance with the measured photophysical data (Table 1).

Example 3

Imaging

Figures 8A, 8B, 8C, 8D, 8E, 8F:
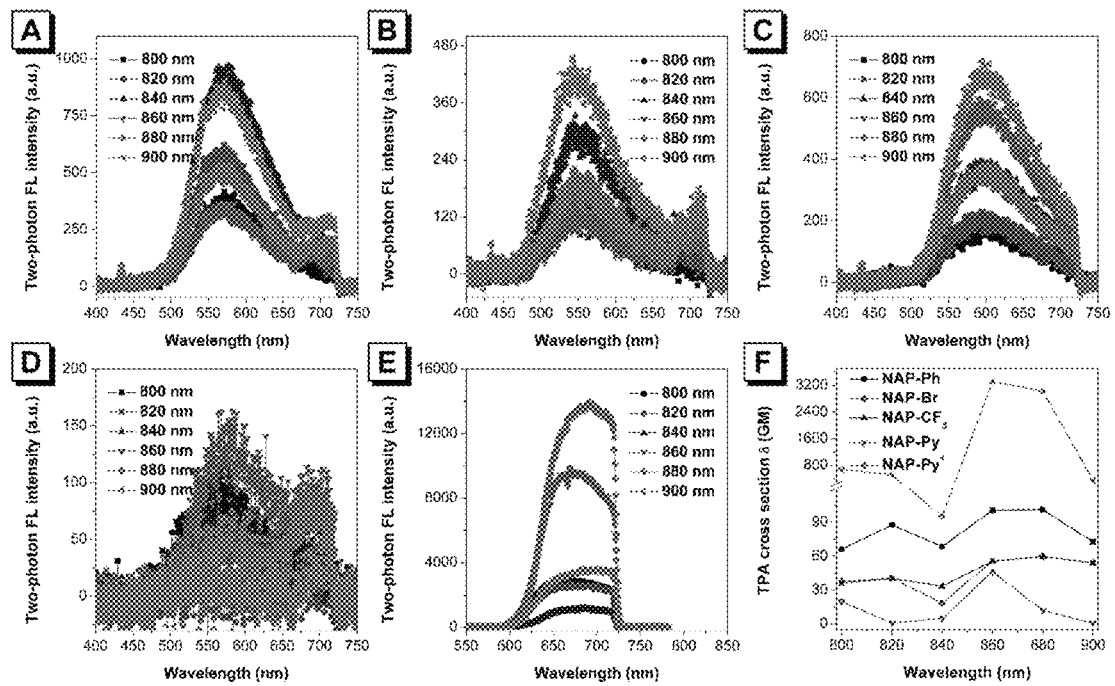
FIG. 8A depicts two-photon excited fluorescence spectra of NAP-Ph in aggregate suspensions.
FIG. 8B depicts two-photon excited fluorescence spectra of NAP-Br in aggregate suspensions.
FIG. 8C depicts two-photon excited fluorescence spectra of NAP-$CF_3$ in aggregate suspensions.
FIG. 8D depicts two-photon excited fluorescence spectra of NAP-Py in aggregate suspensions.
FIG. 8E depicts two-photon excited fluorescence spectra of NAP-Py+ in aggregate suspensions.
FIG. 8F depicts TPA cross sections (δ) of aggregate suspensions of NAP AIEgens in $H_2O$ containing 10% THF (NAP-Ph, NAP-Br, NAP-$CF_3$, and NAP-Py) or 1% $CH_3CN$ (NAP-Py$^+$) (1 GM=$10^{-50}$ cm$^4$ s/photon).
Figure 9:
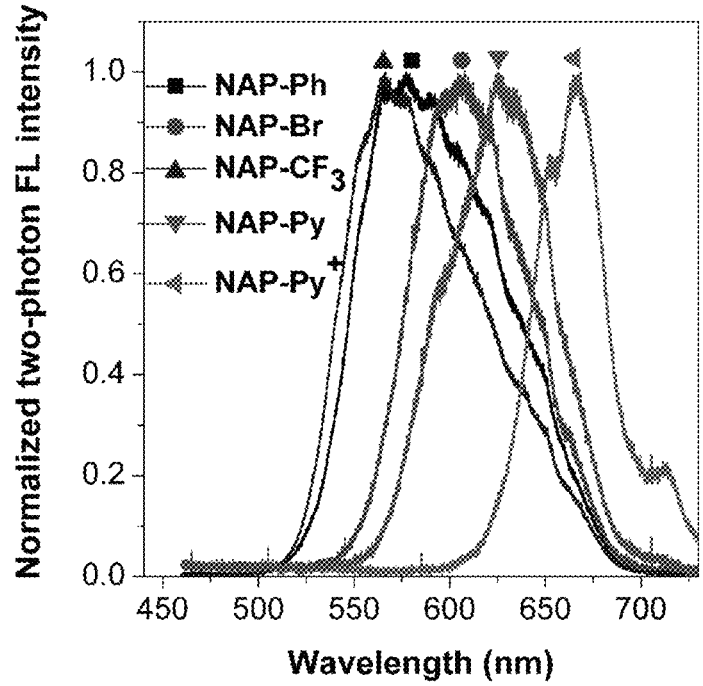
FIG. 9 depicts two-photon excited fluorescence spectra of NAP AIEgens in the solid state under excitation of 800 nm (intensity of about 0.35 mW).

NAP AIEgens possess conjugated D-A structures based on the naphthalene unit as well as TPA properties. To demonstrate this, the TPEF of these NAP AIEgens in aggregate suspensions in H$_2$O containing 10% THF (NAP-Ph, NAP-Br, NAP-CF$_3$, and NAP-Py) or 1% CH$_3$CN (NAP-Py$^+$) and excited with a femtosecond pulsed laser source (800-900 nm) were measured. As shown in FIGS. 8A-8E, the TPEF of NAP AIEgens, and the fluorescence spectra were similar to that excited with one-photon mode, revealing the same excited state for the radiative decay processes. With fluorescein as the standard, the TPA cross sections (δ) of NAP AIEgens at different wavelengths were also measured (FIG. 8F). NAP-Ph, NAP-Br, NAP-CF$_3$, and NAP-Py exhibited moderate TPA cross section (δ) values of about 45-100 GM at 860 nm, which were larger than that of fluorescein. NAP-Py$^+$ possessed a very large TPA cross section (δ) value due to its large conjugation and strong ICT effect. To further acquire the TPEF, NAP AIEgens in solid states were directly excited at 800 nm (intensity of about 0.35 mW). As shown in FIG. 9, even under very low excitation, strong TPEF spectra of NAP AIEgens can be obtained. These data revealed that NAP AIEgens can be applied for two-photon fluorescence imaging.

Figure 10:
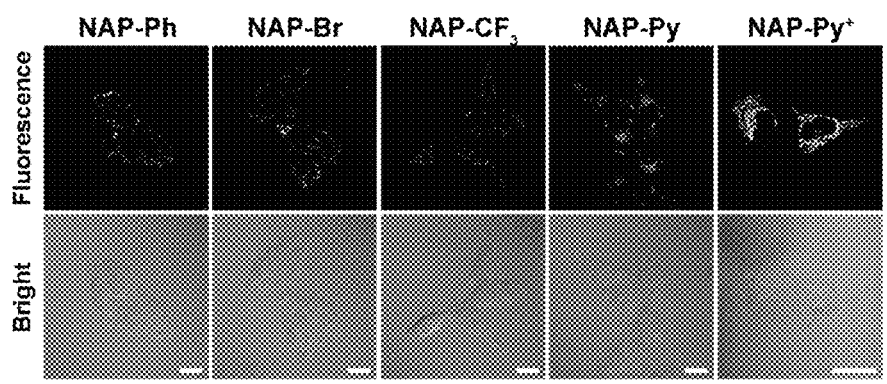
FIG. 10 depicts CLSM images of HeLa cells incubated with NAP-Ph (100 nM), NAP-Br (100 nM), NAP-CF$_3$ (100 nM), NAP-Py (100 nM), and NAP-Py$^+$ (1 μM). Scale bar: 20 μm.
Figure 11:
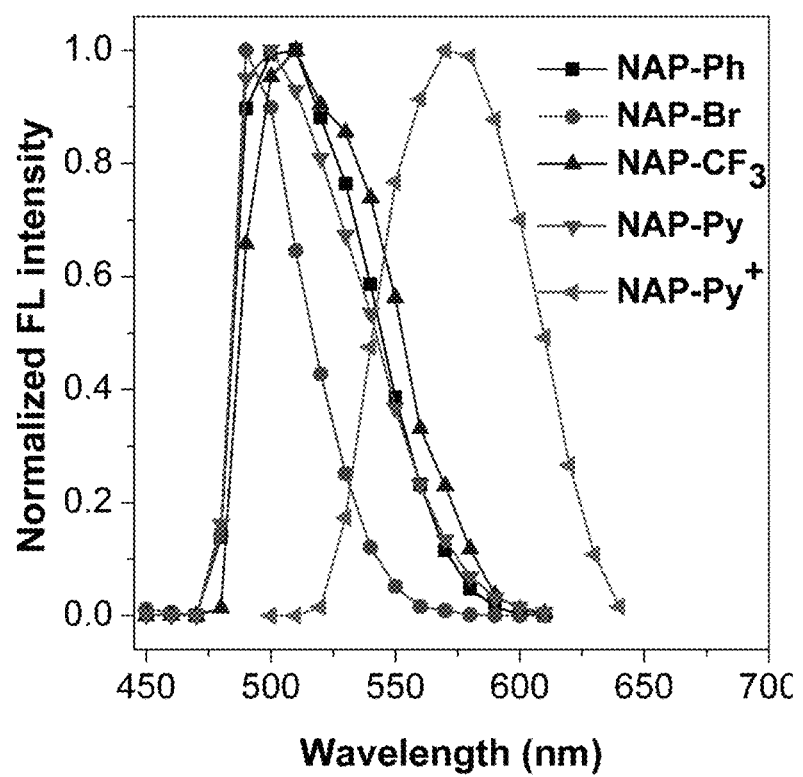
FIG. 11 depicts in situ fluorescence spectra of NAP AIEgens in HeLa cells.

One-photon cell imaging experiments were performed by confocal laser scanning microscopy (CLSM) to evaluate the biological applications of NAP AIEgens. After incubation in HeLa cells for 15 min, bright fluorescence of NAP AIEgens in cytoplasm was obtained (FIG. 10), indicating their excellent membrane permeability. In situ fluorescence spectra of NAP AIEgens in HeLa cells were acquired by using the Lambda mode (FIG. 11). The in situ fluorescence of NAP AIEgens in live cells showed a blue-shift feature, probably due to their ICT effect.

Figure 12:
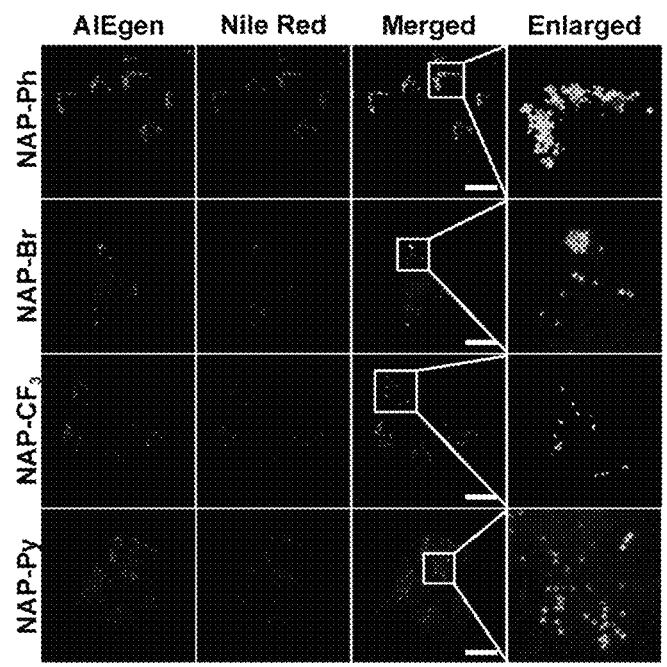
FIG. 12 depicts CLSM images of HeLa cells incubated with NAP-Ph, NAP-Br, NAP-CF$_3$, NAP-Py and Nile Red. Concentration: 100 nM. Scale bar: 20 μm.
Figure 13:
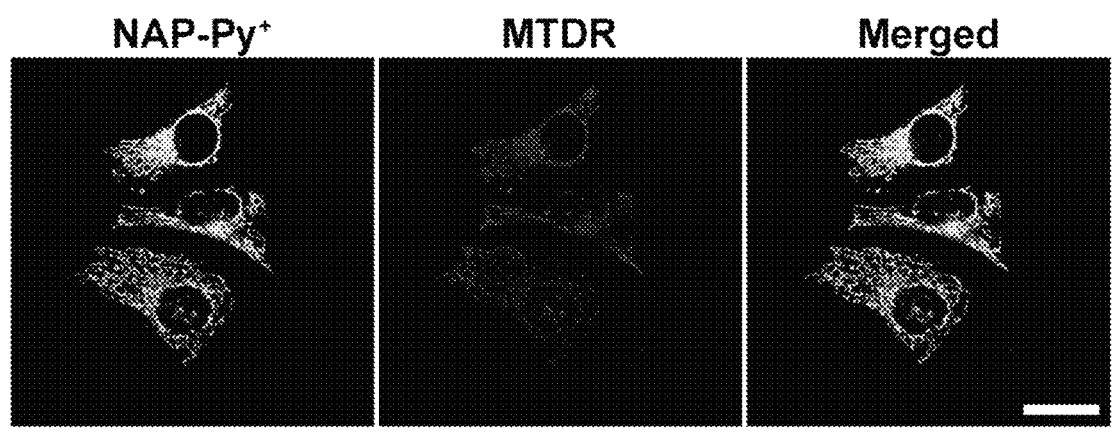
FIG. 13 depicts confocal fluorescence microscopy images of HeLa cells incubated with NAP-Py$^+$ (1 μM) and MitoTraker Deep Red (MTDR, 100 nM). Scale bar: 20 μm.

To confirm the intracellular location of NAP AIEgens in live cells, co-staining imaging experiments were performed. NAP-Ph, NAP-Br, NAP-CF$_3$, and NAP-Py showed distributions in HeLa cells similar to the commercial LDs dye Nile Red (FIG. 12), and the corresponding Pearson's coefficient for NAP-Ph, NAP-Br, NAP-CF$_3$, and NAP-Py were 0.90, 0.83, 0.85 and 0.88, respectively, indicating that NAP-Ph, NAP-Br, NAP-CF$_3$, and NAP-Py are novel LDs-specific dyes. As for NAP-Py$^+$, it showed high overlap (Pearson's coefficient of 0.89) with commercial mitochondria dye MitoTracker Deep Red FM (FIG. 13). It is believed that positive-charged dyes like NAP-Py$^+$ can stain mitochondria due to the high negative membrane potential of mitochondria. To determine why other NAP AIEgens without positive charge locate in LDs, additional investigation was conducted.

Figure 14:
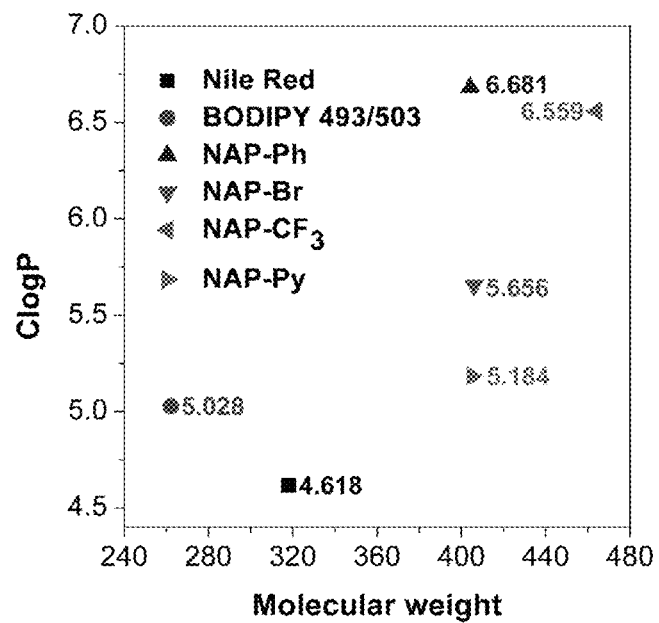
FIG. 14 depicts C log P values of Nile Red, BODIPY 493/503, NAP-Ph, NAP-Br, NAP-CF$_3$, and NAP-Py as a function of molecular weight.

To explain the co-staining data of NAP-Ph, NAP-Br, NAP-CF$_3$, and NAP-Py, basic calculations were conducted. Considering the inherent lipophilic environment of LDs due to triglycerides and cholesterol esters, it was anticipated that lipophilic organic dyes with high hydrophobicity or a high log P (n-octanol/water partition coefficient) value could locate in LDs, which is consistent with the theory of similarity and intermiscibility. Calculated log P (C Log P) values were estimated using ChemBioDraw 14.0. The C Log P values of almost all these LDs dyes were in the range of 3.1-16.643. Previously, Prof. R. W. Horobin's group reported that organic dyes staining LDs usually exhibit the log P value over 5 predicted by using quantitative structure activity relations (QSAR) models. NAP-Ph, NAP-Br, NAP-CF$_3$, and NAP-Py exhibited C Log P values of 5.184-6.681 (FIG. 14), which were higher than the C log P values of commercial LDs dye Nile Red (4.618) and BODIPY 493/503 (5.028). These C log P values probably explain why NAP-Ph, NAP-Br, NAP-CF$_3$, and NAP-Py showed better LDs staining performance than Nile Red. C log P value of NAP-Py$^+$ (0.340) was too low to meet the conditions for LDs staining. These semi-theoretical data further indicated that these lipophilic NAP-Ph, NAP-Br, NAP-CF$_3$, and NAP-Py can specifically locate in LDs.

Figure 15:
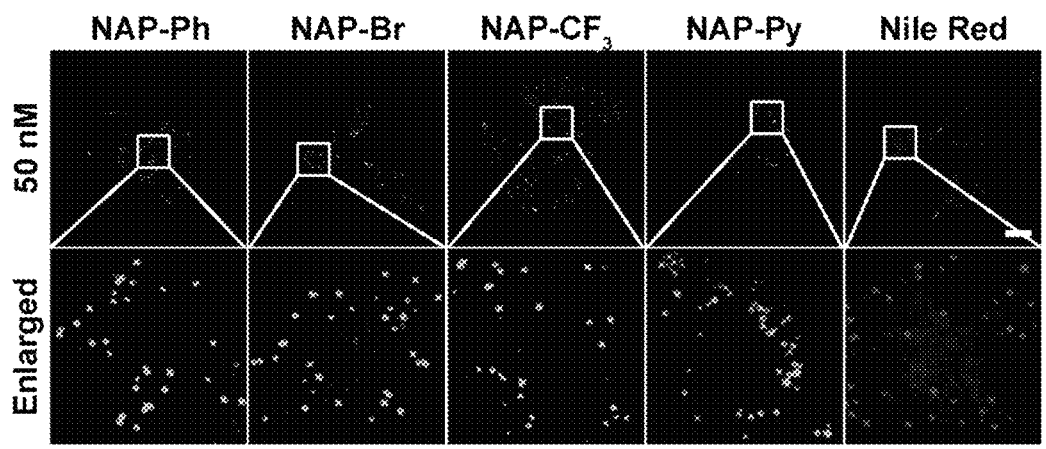
FIG. 15 depicts CLSM images of HeLa cells stained with NAP-Ph, NAP-Br, NAP-CF$_3$, NAP-Py, and Nile Red in HeLa cells. Scale bar: 20 μm.
Figures 16A, 16B, 16C, 16D:
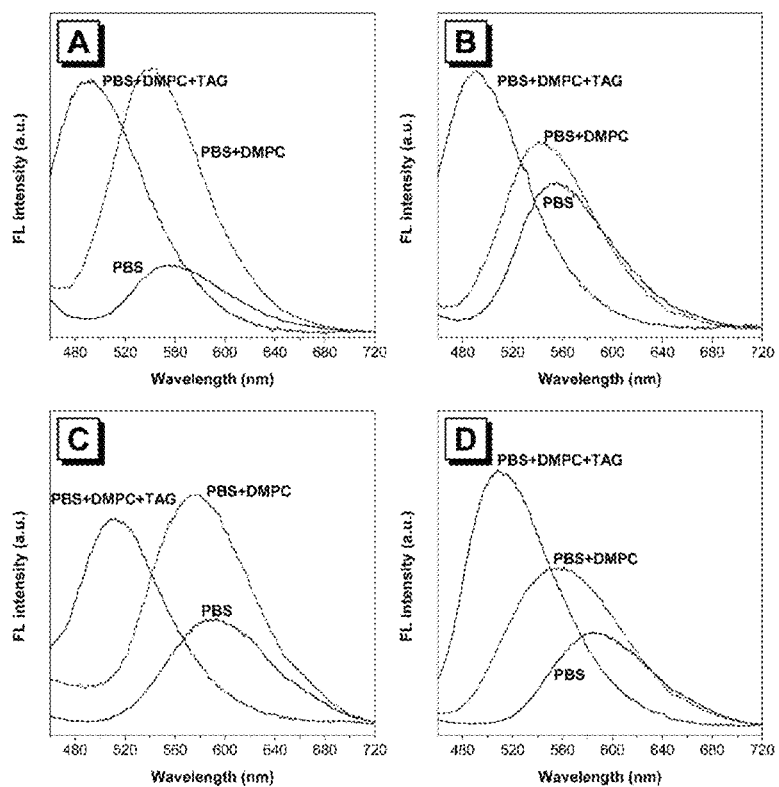
FIG. 16A depicts fluorescence (FL) intensity changes of NAP-Ph.
FIG. 16B depicts fluorescence (FL) intensity changes of NAP-Br.
FIG. 16C depicts fluorescence (FL) intensity changes of NAP-CF$_3$.
FIG. 16D depicts fluorescence (FL) intensity changes of NAP-Py in solutions (pH 7.2) of PBS, PBS with DMPC, and PBS with DMPC and TAG. Concentration: NAP AIEgens of 1 μM, DMPC of 40 μg/mL, TAG of 80 μg/mL.

One-photon imaging experiments in HeLa cells stained with 50 nM of NAP-Ph, NAP-Br, NAP-CF$_3$, and NAP-Py were performed, and Nile Red was used as comparison. Unexpectedly, clear fluorescence of NAP-Ph, NAP-Br, NAP-CF$_3$, and NAP-Py in LDs with quite low background fluorescence was detected at low concentrations (FIG. 15), and the confocal laser intensity (405 nm, intensity of 12%) used was very low. As far as we know, this is the lowest concentration used for LDs imaging. Though Nile Red (50 nM) can also be applied for LDs imaging, it also showed non-specific staining in cytoplasm, resulting in a low signal-to-noise ratio, which is in accord with previous studies. These data demonstrated NAP-Ph, NAP-Br, NAP-CF$_3$, and NAP-Py showed much more outstanding LDs staining capacity than Nile Red. There are probably two reasons for these ultralow concentrations of NAP-Ph, NAP-Br, NAP-CF$_3$, and NAP-Py for LDs-specific staining: One is their inherent lipophilic properties, which were demonstrated by higher C log P values than Nile Red (FIG. 14), resulting in their specific locations in LDs; the other is their enhanced fluorescence in LDs compared with that in solution. To demonstrate the latter reason, the fluorescence changes of NAP-Ph, NAP-Br, NAP-CF$_3$, and NAP-Py in the presence of 1,2-dimyristoyl-sn-glycero-3-phosphocholine (DMPC) and trioleate glycerol (TAG) were investigated. As shown in FIGS. 16A-16D, the fluorescence of NAP-Ph, NAP-Br, NAP-CF$_3$, and NAP-Py with DMPC and TAG blue shifted and their intensity was also enhanced (about 1.7~3.6 fold) compared with those in PBS (pH=7.2), resulting in their enhanced fluorescence in live cells and low incubation concentration for specific LDs staining. This explains why the in situ fluorescence of these AIEgens in live cells showed the blue-shift feature (FIGS. 10-11).

Figure 17:
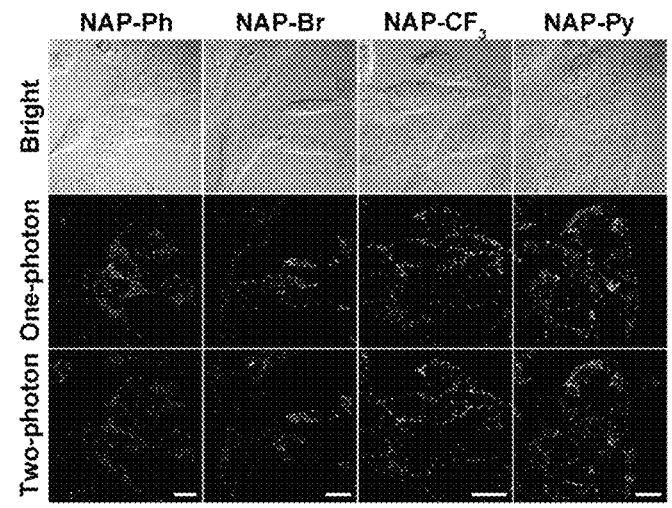
FIG. 17 depicts one-photon ($\lambda_{ex}$=405 nm) and two-photon ($\lambda_{ex}$=860 nm) fluorescence microscopy images of HeLa cells stained with NAP-Ph, NAP-Br, NAP-CF$_3$, and NAP-Py in HeLa cells. Concentration: 100 nM. Scale bar: 20 μm.

NAP-Ph, NAP-Br, NAP-CF$_3$, and NAP-Py displayed good TP excited fluorescence with moderate TPA cross sections (45-100 GM at 860 nm). The successful application of these AIEgens for specific LDs staining in live cells with one-photon microscopy prompted investigating the utility of these compounds in the TP mode. Two-photon fluorescence imaging of these NAP AIEgens in HeLa cells with an 860-nm femtosecond pulsed laser was performed. As shown in FIG. 17, bright green fluorescence of LDs in live cells was obtained by TP excitation of 860 nm, which was almost identical with that under one-photon excitation of 405 nm. These data showed that NAP-Ph, NAP-Br, NAP-CF$_3$, NAP-Py show great potential in TP fluorescence imaging.

Figure 18:
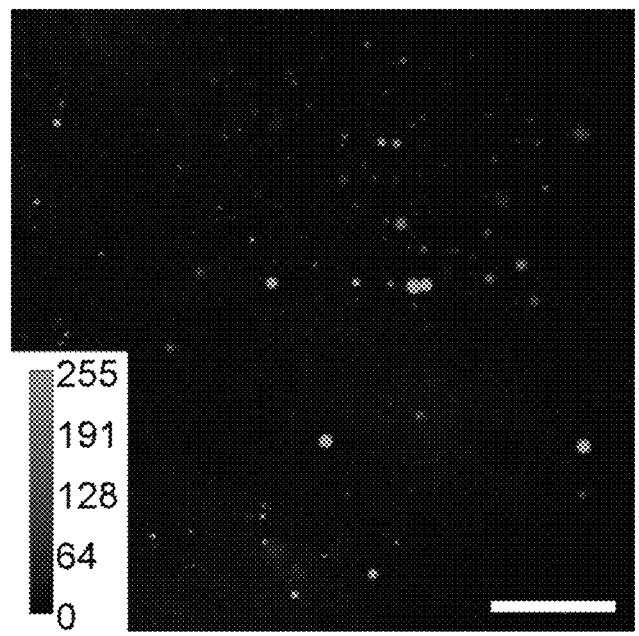
FIG. 18 depicts ex vivo two-photon ($\lambda_{ex}$=860 nm) images of live mice liver tissue incubated with NAP-CF$_3$ (1 μM). Scale bar: 20 μm.
Figures 19A, 19B, 19C, 19D, 19E, 19F, 19G, 19H:
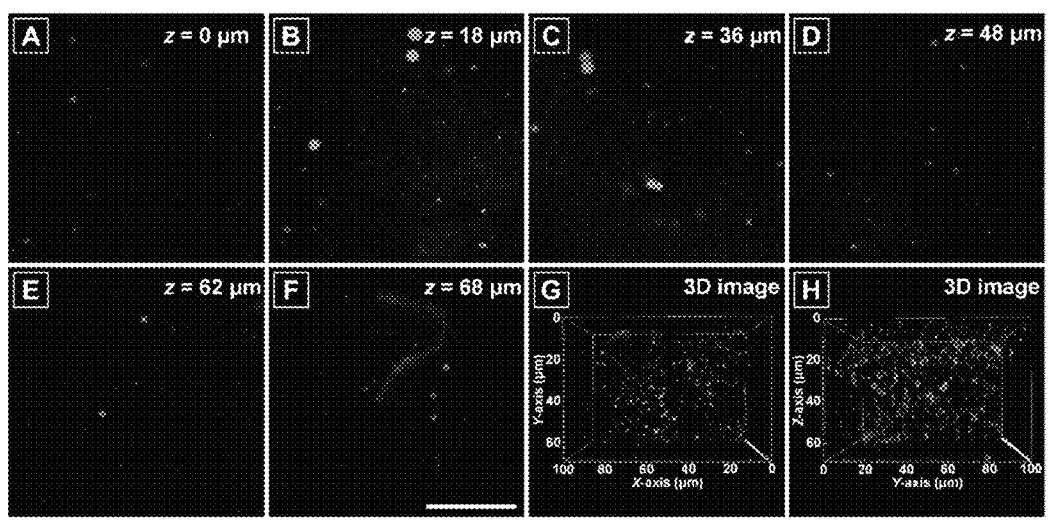
FIGS. 19A-19F depict ex vivo two-photon ($\lambda_{ex}$=860 nm) images of the mice liver tissue stained with NAP-CF$_3$ (1 μM) at different penetration depths. Scale bar: 20 μm.
FIGS. 19G-19H depict reconstructed 3D two-photon images along different axes.

TP fluorescence imaging outperforms imaging in one-photon mode as a result of high penetration in tissues and low background fluorescence because of near-infrared light excitation and low excitation power. To further demonstrate these merits, ex vivo TP imaging of live mice liver tissue incubated with NAP-CF$_3$ was carried out. After incubation with NAP-CF$_3$ (1 µM) for 1 h, bright spherical spots with TP fluorescence of NAP-CF$_3$ were observed (FIG. 18). For the live mice liver tissue without NAP-CF$_3$, however, only low background fluorescence was obtained. These data revealed that NAP-CF$_3$ also displayed excellent LDs staining property in live mice liver tissue with quite low background fluorescence. To investigate whether NAP-CF$_3$ could show LDs-specific staining in deep live mice liver tissue, TP fluorescence images along the Z-axis were captured. As shown in FIGS. 19A-19F, the fluorescent signal of the spherical spot could be clearly detected at different Z-axis depths even up to 70 µm. In addition, 3D two-photon fluorescence images with high resolution along different visual directions were successfully reconstructed (FIGS. 19G-19H), which further clearly demonstrated the high penetration and high signal-to-noise ratio of TP imaging of NAP-CF$_3$. These excellent TP tissue imaging properties render NAP-CF$_3$ a tremendous tool to visualize LDs-associated biomedical application in live tissues.

Example 4

Photostability and Cytotoxicity

Figure 20:
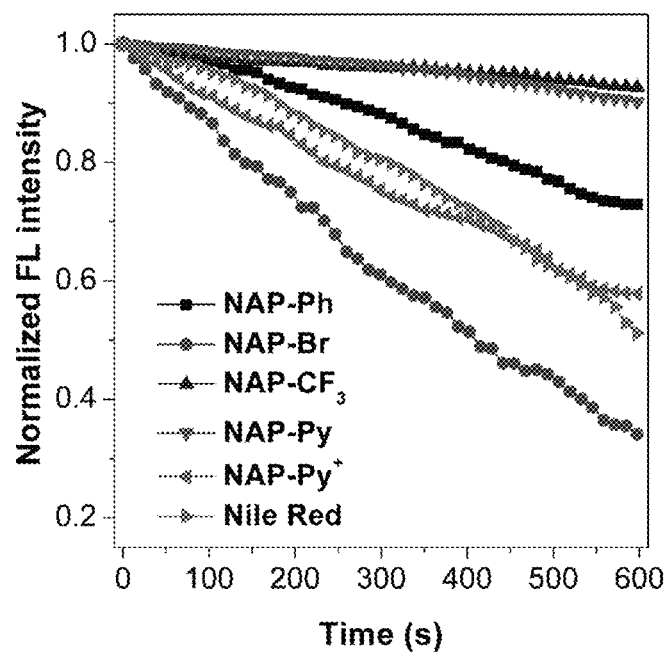
FIG. 20 is a graph depicting photostability of NAP AIEgens and Nile Red in HeLa cells under continuous irradiation (irradiation conditions: for NAP AIEgens, 405 nm laser, laser power of 12%; for Nile Red, 543 nm laser, laser power of 12%).
Figures 21A, 21B:
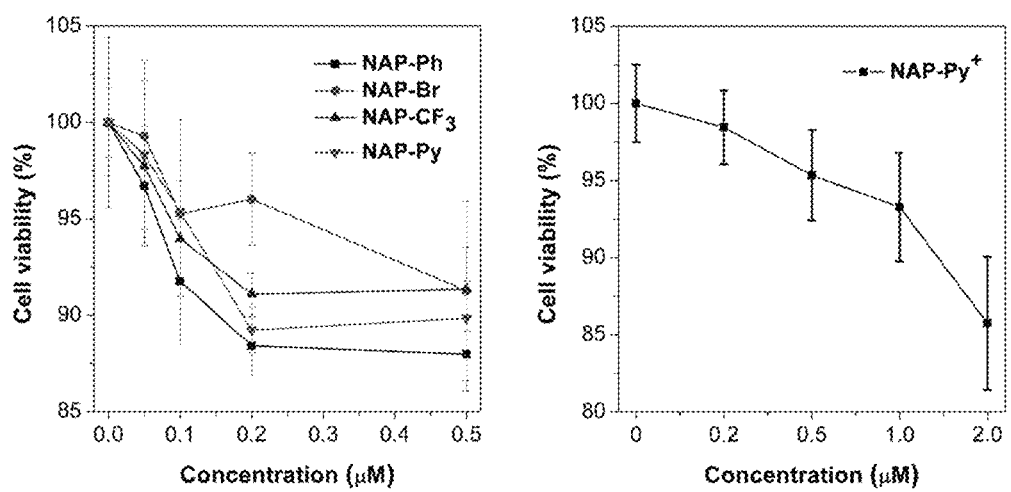
FIG. 21A is a graph depicting the cytotoxicity of NAP-Ph, NAP-Br, NAP-CF$_3$, and NAP-Py in HeLa cells.
FIG. 21B is a graph depicting the cytotoxicity of NAP-Py$^+$ in HeLa cells.
Figure 22:
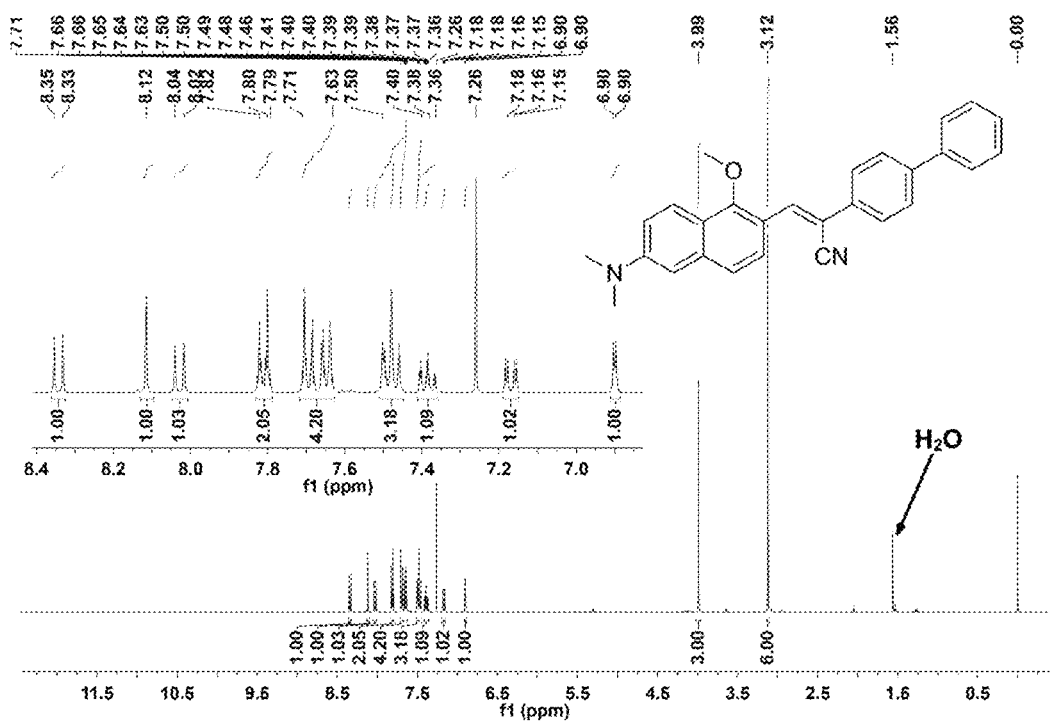
FIG. 22 depicts $^1$H NMR (400 MHz, CDCl$_3$) spectrum of NAP-Ph.
Figure 23:
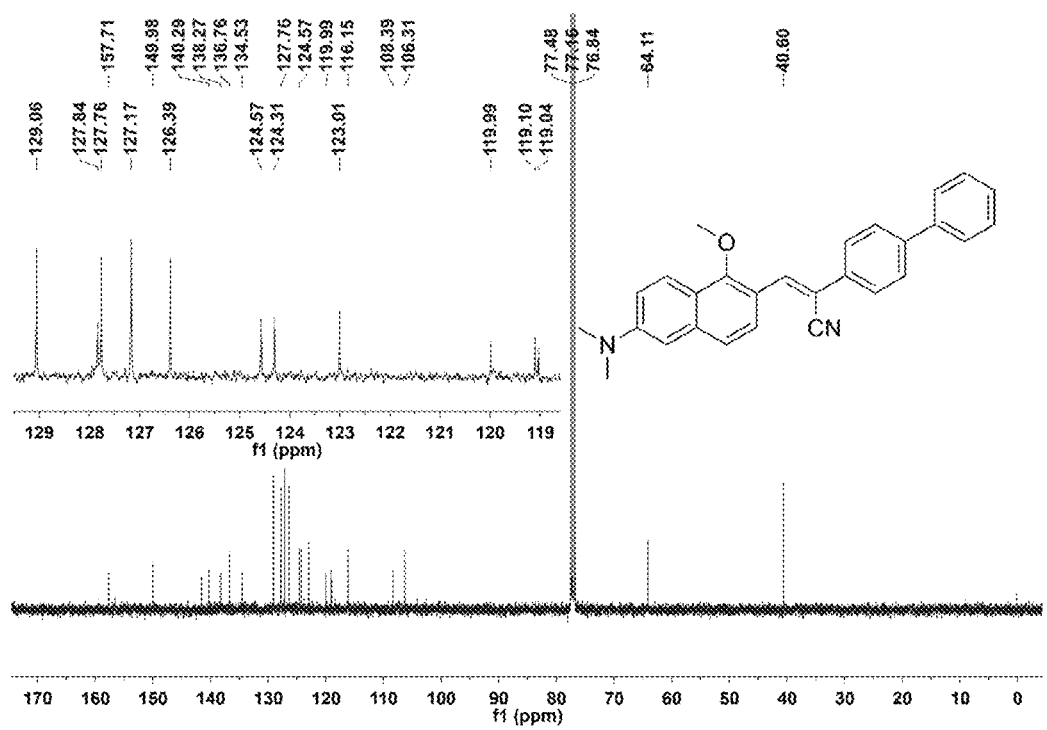
FIG. 23 depicts $^{13}$C NMR (100 MHz, CDCl$_3$) spectrum of NAP-Ph.
Figure 24:
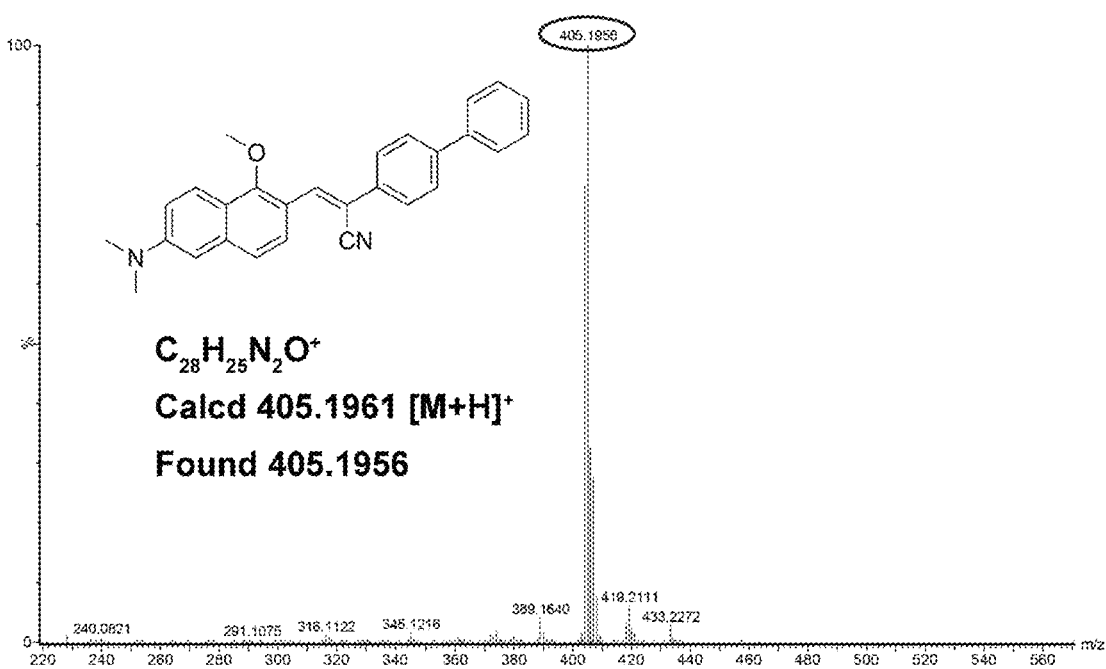
FIG. 24 depicts MALDI-TOF-HRMS spectrum of NAP-Ph.
Figure 25:
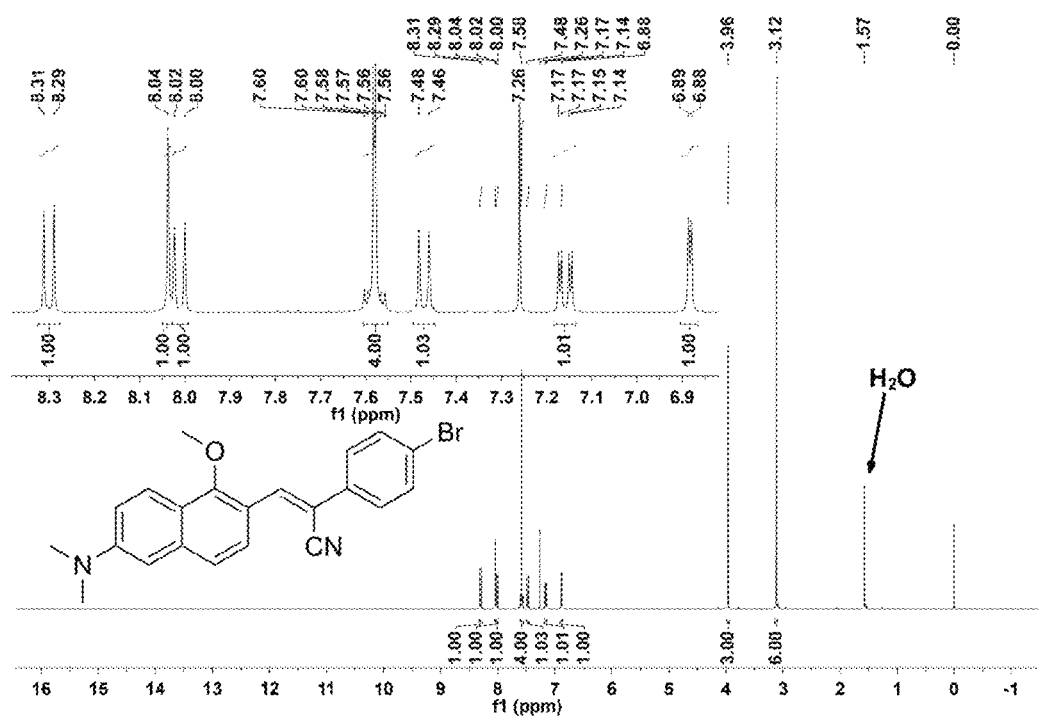
FIG. 25 depicts $^1$H NMR (400 MHz, CDCl$_3$) spectrum of NAP-Br.
Figure 26:
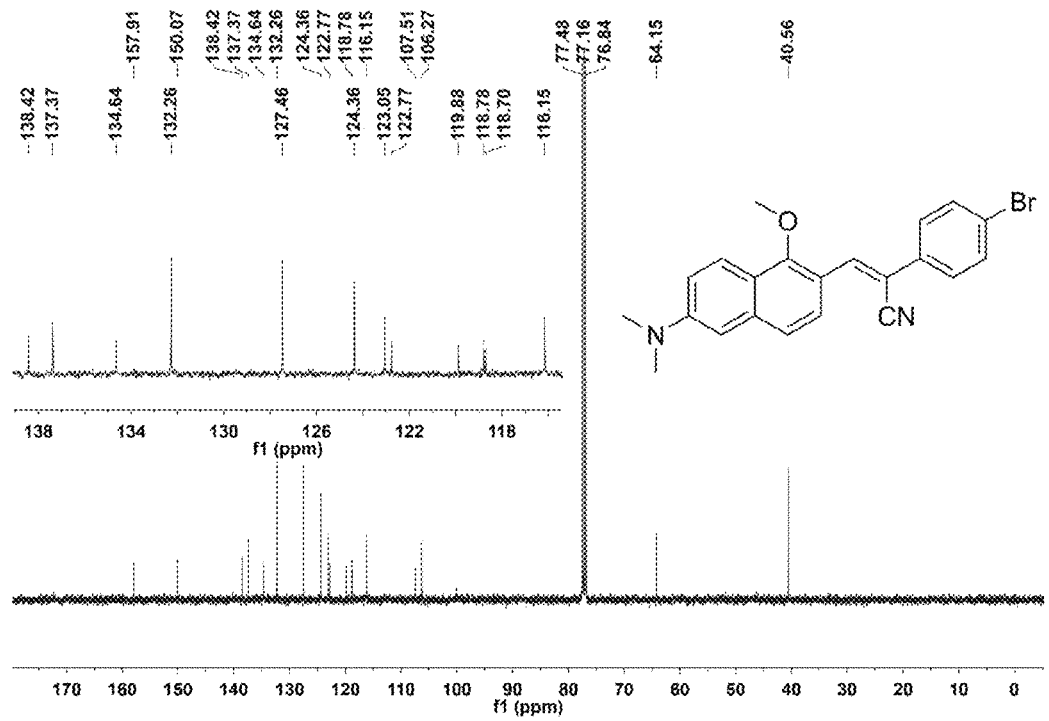
FIG. 26 depicts $^{13}$C NMR (100 MHz, CDCl$_3$) spectrum of NAP-Br.
Figure 27:
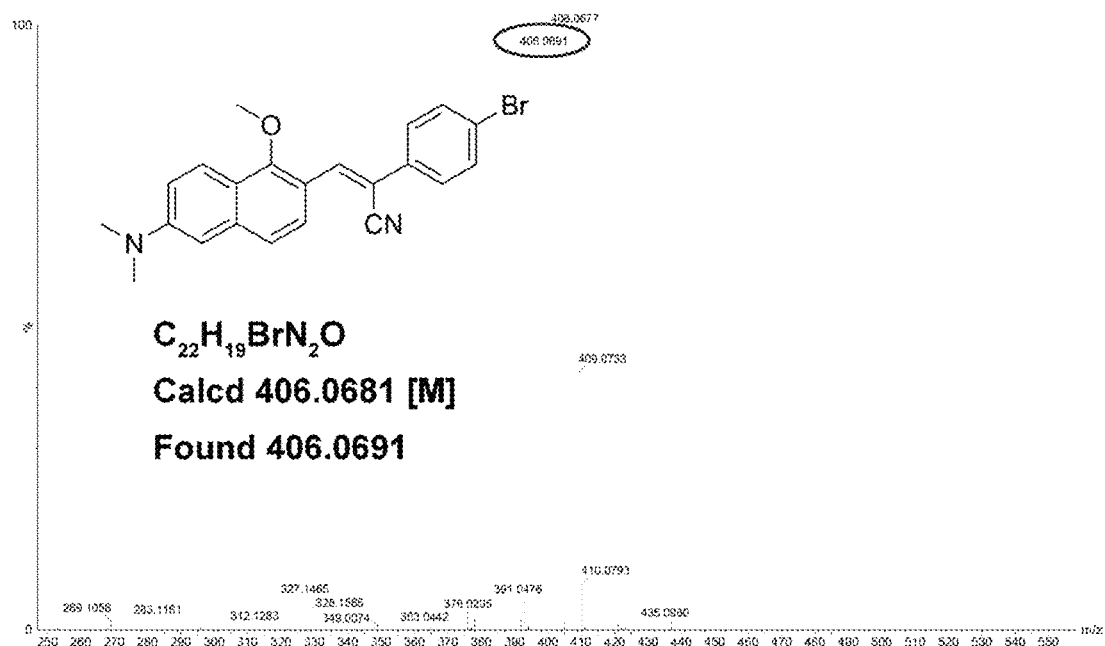
FIG. 27 depicts MALDI-TOF-HRMS spectrum of NAP-Br.
Figure 28:
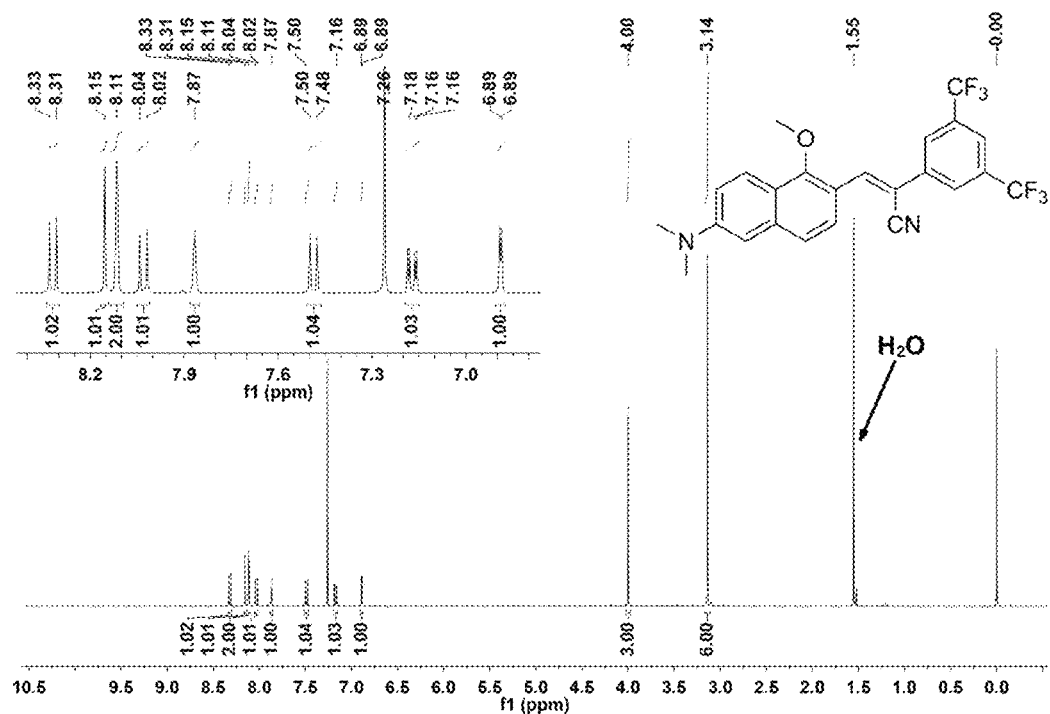
FIG. 28 depicts $^1$H NMR (400 MHz, CDCl$_3$) spectrum of NAP-CF$_3$.
Figure 29:
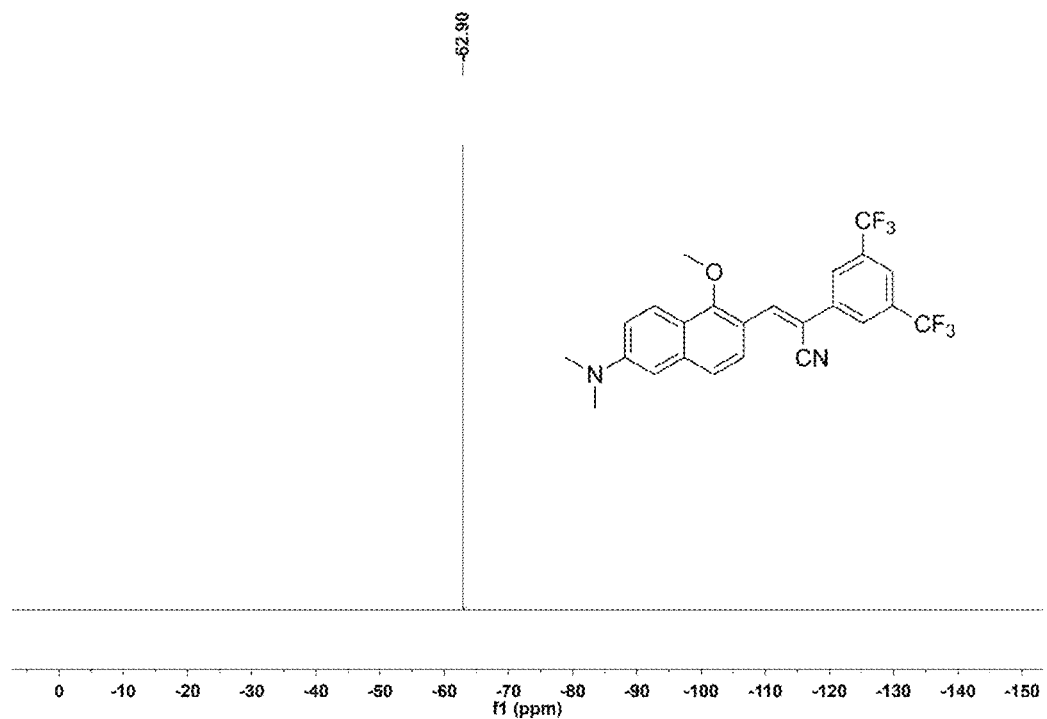
FIG. 29 depicts $^{19}$F NMR (376 MHz, CDCl$_3$) spectrum of NAP-CF$_3$.
Figure 30:
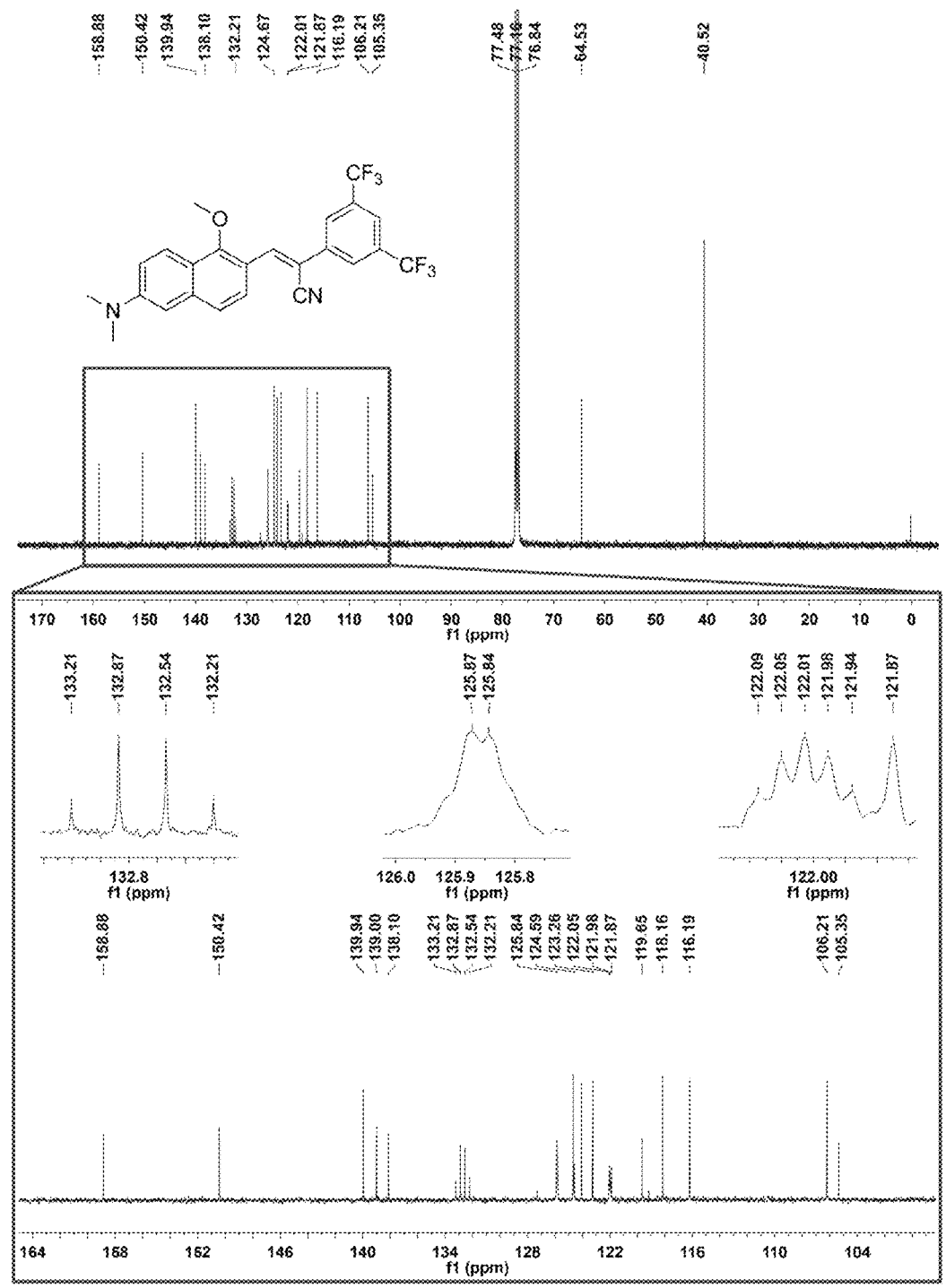
FIG. 30 depicts $^{13}$C NMR (100 MHz, CDCl$_3$) spectrum of NAP-CF$_3$.
Figure 31:
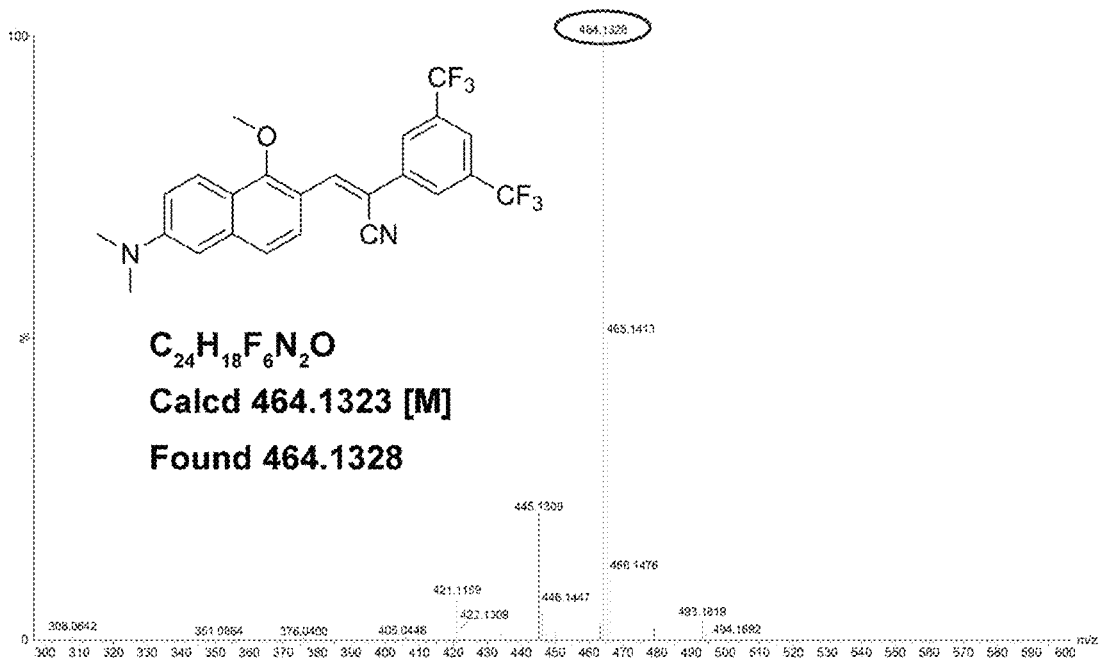
FIG. 31 depicts MALDI-TOF-HRMS spectrum of NAP-CF$_3$.
Figure 32:
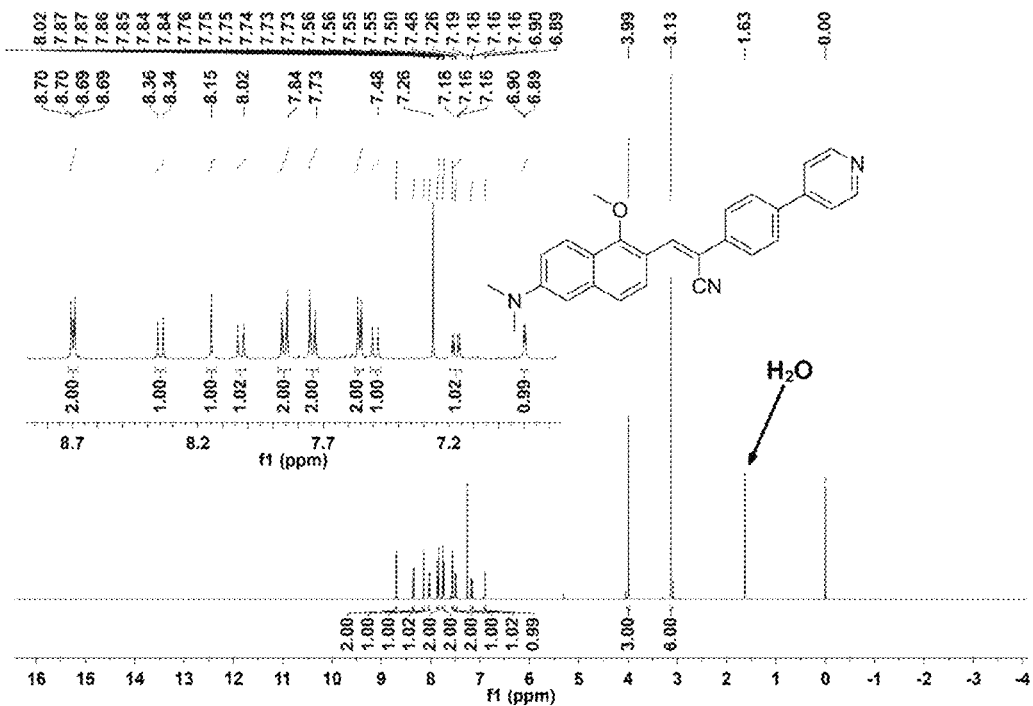
FIG. 32 depicts $^1$H NMR (400 MHz, CDCl$_3$) spectrum of NAP-Py.
Figure 33:
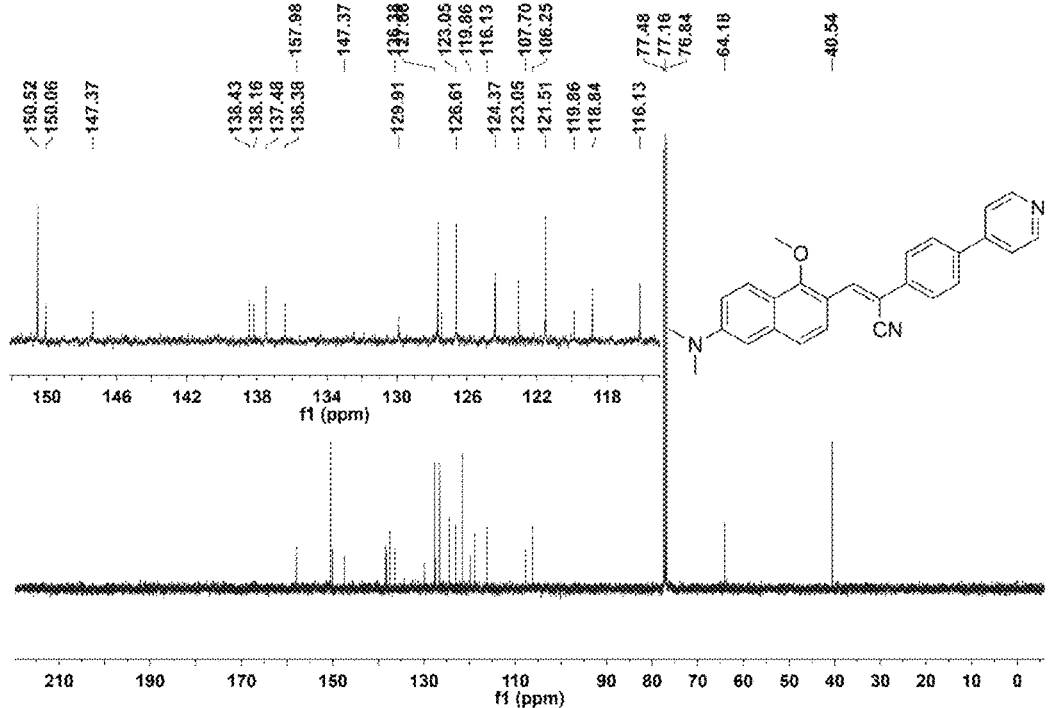
FIG. 33 depicts $^{13}$C NMR (100 MHz, CDCl$_3$) spectrum of NAP-Py.
Figure 34:
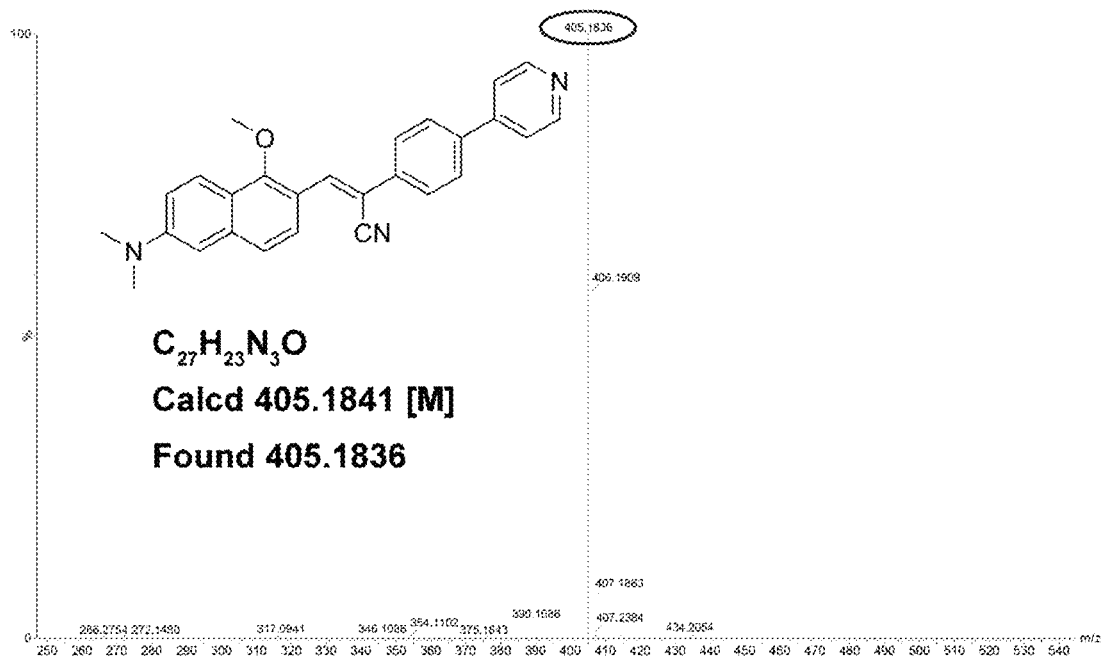
FIG. 34 depicts MALDI-TOF-HRMS spectrum of NAP-Py.
Figure 35:
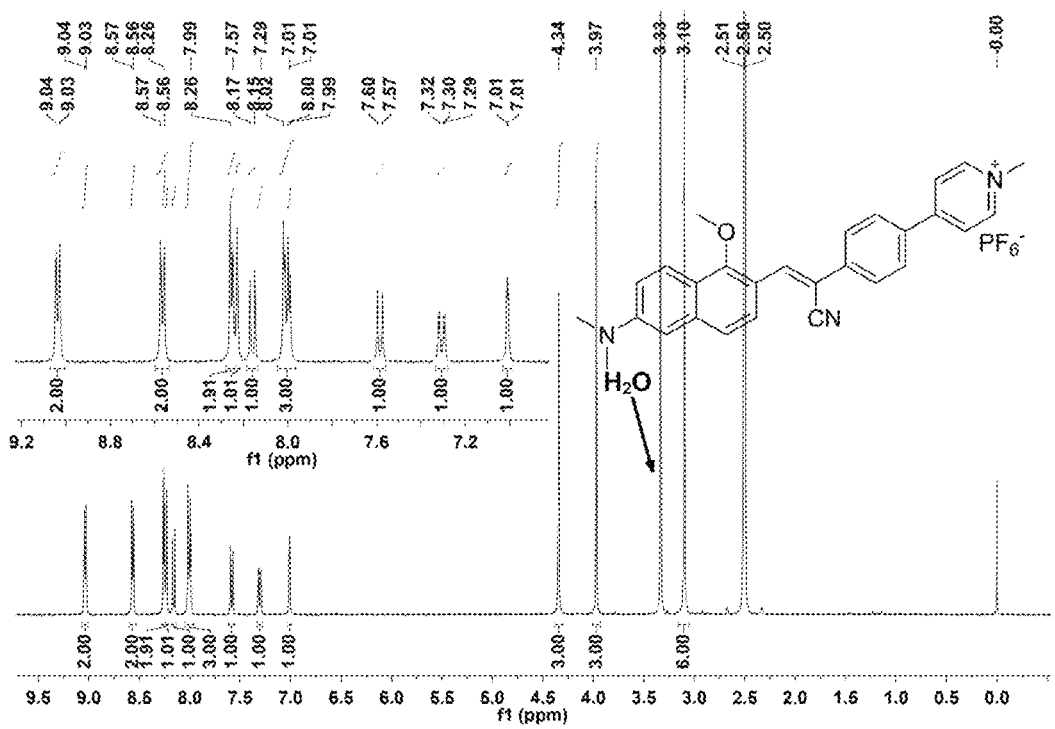
FIG. 35 depicts $^1$H NMR (400 MHz, DMSO-d$_6$) spectrum of NAP-Py$^+$.
Figure 36:
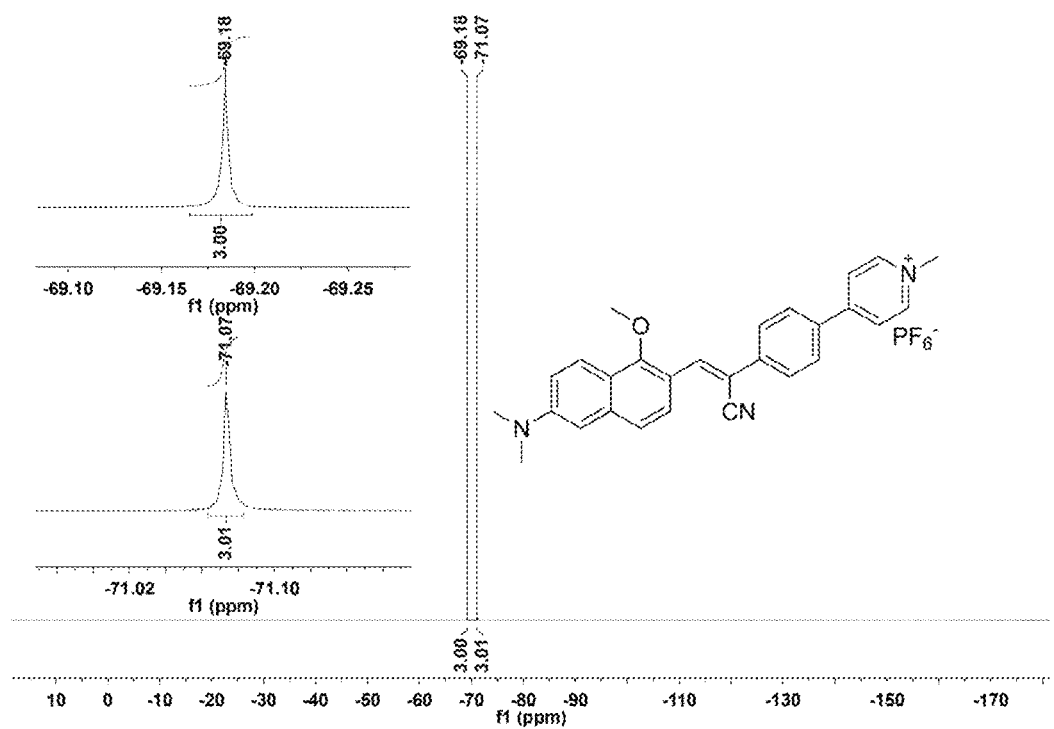
FIG. 36 depicts $^{19}$F NMR (376 MHz, DMSO-d$_6$) spectrum of NAP-Py$^+$.
Figure 37:
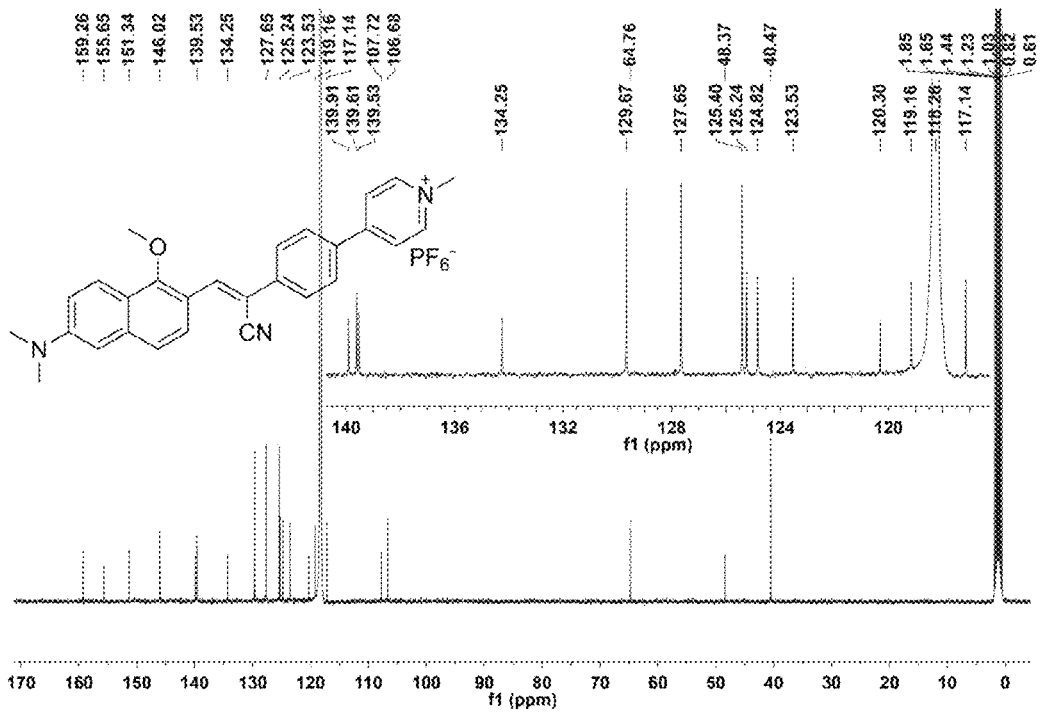
FIG. 37 depicts $^{13}$C NMR (100 MHz, CD$_3$CN) spectrum of NAP-Py$^+$.
Figure 38:
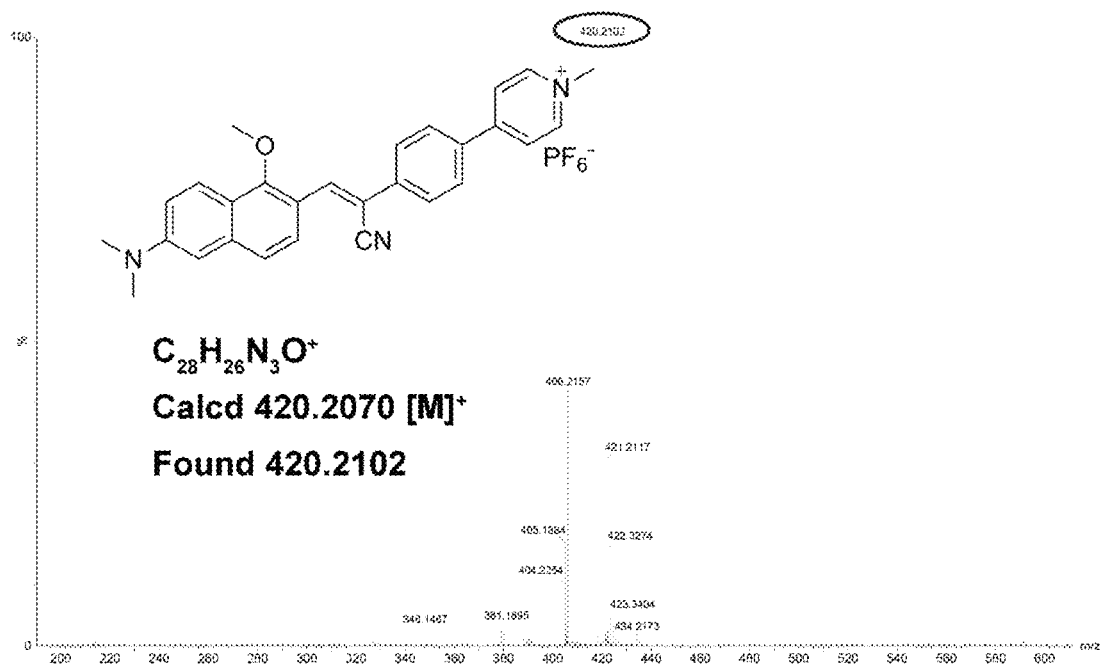
FIG. 38 depicts MALDI-TOF-HRMS spectrum of NAP-Py$^+$.

Considering the above-mentioned excellent bioimaging characteristics of these NAP AIEgens, further experiments were performed to evaluate their photostability and cytotoxicity. The photostability of NAP AIEgens was evaluated by continuous irradiation with confocal lasers, and data was collected every second. After continuous irradiation for 10 min., over 90% of the initial fluorescence intensities of NAP-CF$_3$ and NAP-Py still remained, while the intensity signals of NAP-Ph, NAP-Br and NAP-Py+ dropped to some extent (FIG. 20). In comparison, the fluorescence intensity of Nile Red was drastically decreased. These data indicated that NAP-CF3 and NAP-Py could be used for long-term monitoring of the dynamic changes of LDs in biological samples. Furthermore, standard MTT (3-(4,5-dimethylthiazol-2-yl)-2,5-diphenyl-2H-tetrazolium) assays were performed to evaluate the cytotoxicity of NAP AIEgens in live cells. As seen in FIG. 21, after incubation in HeLa cells for 24 h, the viabilities of HeLa cells were very high and these NAP AIEgens exhibited negligible cytotoxicity within the tested concentrations. These data indicated that NAP AIEgens are biocompatible with biological samples.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A fluorescent compound exhibiting aggregation induced emission properties, the compound having the following backbone structural formula:

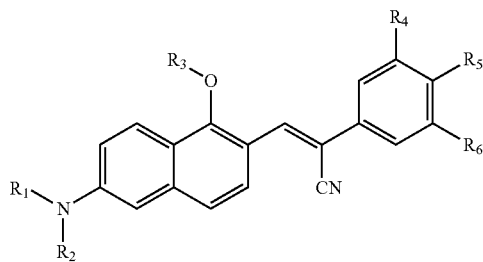

wherein $R_1$, $R_2$, and $R_3$ are independently selected from the group consisting of $C_nH_{2n+1}$, $C_6H_5$, $C_{10}H_7$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$ and

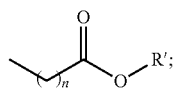

wherein R' is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

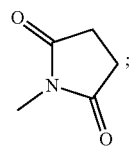

wherein $R_4$, $R_5$, and $R_6$ are independently selected from the group consisting of H, $CH_3$, F, Cl, Br, I, CN, $CF_3$, $NO_2$, Ph, Py, CH=CHPh, and C≡CPh; and wherein n is an integer ranging from 1 to 10.

2. The compound according to claim 1, wherein the compound comprises one or more compounds selected from the group consisting of:

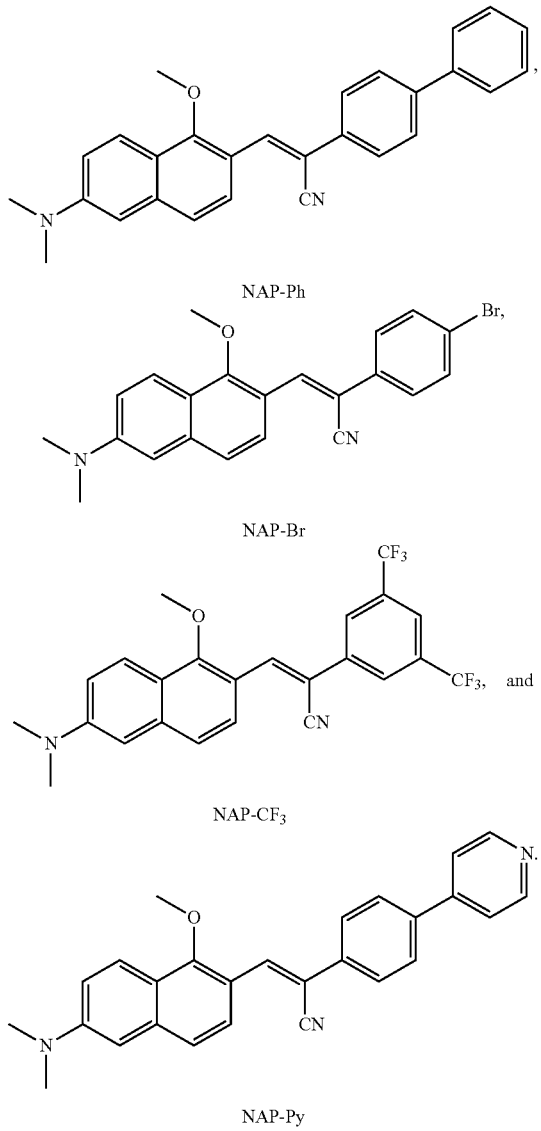

3. A method of cellular imaging, comprising:
contacting a target cell with the compound of claim 1; and
identifying a target of interest in the target cell using an imaging method.

4. The method of claim 3, wherein the target of interest comprises lipid droplets.

5. The method of claim 3, wherein the imaging method is selected from the group consisting of fluorescence microscopy and confocal laser scanning microscopy.

6. The method of claim 5, wherein the fluorescence microscopy comprises two-photon fluorescence imaging.

7. The method of claim 3, wherein the target cell is a live cell.

8. The method of claim 7, wherein the target cell is in live tissue.

9. The method of claim 3, wherein a concentration of the compound is 50 nM or less.

10. A fluorescent compound exhibiting aggregation induced emission properties, the compound comprising one or more compounds selected from the group consisting of:

NAP-Ph

NAP-Br

NAP-CF₃

NAP-Py

11. A method of cellular imaging, comprising:
contacting a target cell with the compound of claim 10; and
identifying a target of interest in the target cell using an imaging method.

12. The method of claim 11, wherein the target of interest comprises lipid droplets.

13. The method of claim 11, wherein the imaging method is selected from the group consisting of fluorescence microscopy and confocal laser scanning microscopy.

14. The method of claim 11, wherein the fluorescence microscopy comprises two-photon fluorescence imaging.

15. The method of claim 11, wherein the target cell is a live cell.

16. The method of claim 15, wherein the target cell is in live tissue.

17. The method of claim 11, wherein a concentration of the compound is 50 nM or less.

18. A method of cellular imaging, comprising:
contacting a target cell with a compound having the following backbone structural formula wherein $R_1$, $R_2$, and $R_3$ are independently selected from the group consisting of $C_nH_{2n+1}$, $C_6H_5$, $C_{10}H_7$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$ and wherein R' is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and wherein $R_4$, $R_5$, and $R_6$ are independently selected from the group consisting of H, $CH_3$, F, Cl, Br, I, CN, $CF_3$, $NO_2$, Ph, Py, CH=CHPh, and C≡CPh; and
wherein n is an integer ranging from 1 to 10; and
identifying a target of interest in the target cell using an imaging method.

19. The method according to claim 18, wherein the compound comprises one or more compounds selected from the group consisting of:

NAP-Ph

NAP-Br

-continued
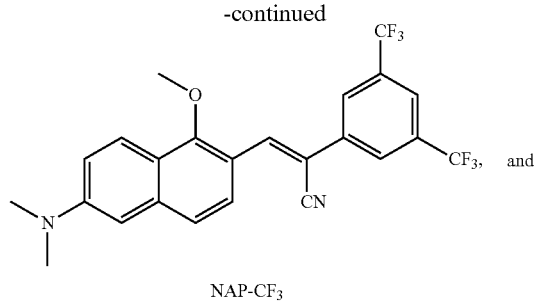
NAP-CF₃
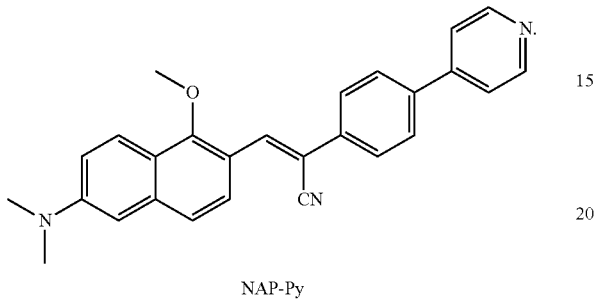
NAP-Py
20. The method according to claim 18, wherein the target of interest comprises lipid droplets.
* * * * *